(12) United States Patent
Knopp

(10) Patent No.: US 7,658,610 B2
(45) Date of Patent: *Feb. 9, 2010

(54) SYSTEMS AND METHODS FOR FABRICATING A DENTAL TEMPLATE WITH A 3-D OBJECT PLACEMENT

(75) Inventor: Peter G. Knopp, Palo Alto, CA (US)

(73) Assignee: Align Technology, Inc., Santa Clara, CA (US)

(*) Notice: Subject to any disclaimer, the term of this patent is extended or adjusted under 35 U.S.C. 154(b) by 567 days.

This patent is subject to a terminal disclaimer.

(21) Appl. No.: 10/794,324

(22) Filed: Mar. 4, 2004

(65) Prior Publication Data

US 2004/0229185 A1    Nov. 18, 2004

Related U.S. Application Data

(63) Continuation-in-part of application No. 10/375,223, filed on Feb. 26, 2003, now abandoned.

(51) Int. Cl.
*A61C 3/00* (2006.01)
(52) U.S. Cl. ........................................ 433/24
(58) Field of Classification Search ................ 433/24, 433/29, 6
See application file for complete search history.

(56) References Cited

U.S. PATENT DOCUMENTS

| | | | |
|---|---|---|---|
| 2,467,432 A | 4/1949 | Kesling | |
| 3,660,900 A | 5/1972 | Andrews | |
| 3,860,803 A | 1/1975 | Levine | |
| 3,916,526 A | 11/1975 | Schudy | |
| 3,950,851 A | 4/1976 | Bergersen | |
| 4,014,096 A | 3/1977 | Dellinger | |
| 4,195,046 A | 3/1980 | Kesling | |
| 4,324,546 A | 4/1982 | Heitlinger et al. | |
| 4,348,178 A | 9/1982 | Kurz | |
| 4,478,580 A | 10/1984 | Barrut | |
| 4,504,225 A | 3/1985 | Yoshii | |
| 4,505,673 A | 3/1985 | Yoshii | |
| 4,551,096 A | 11/1985 | Dellinger | |
| 4,575,805 A | 3/1986 | Moermann et al. | |
| 4,611,288 A | 9/1986 | Duret et al. | |

(Continued)

FOREIGN PATENT DOCUMENTS

EP    0091876 A1    10/1983

(Continued)

OTHER PUBLICATIONS

Alexander et al., "The DigiGraph Work Station Part 2, Clinical Management," *JCO* (Jul. 1990), pp. 402-407.

(Continued)

*Primary Examiner*—Ralph A Lewis
(74) *Attorney, Agent, or Firm*—Townsend and Townsend and Crew LLP

(57) ABSTRACT

A dental template to position an object on a patient's tooth includes digitizing the patient's tooth; adding virtual objects to predetermined three-dimensional positions on the digitized tooth; and fabricating the dental template to locate the object at the predetermined 3D position on the patient's tooth. The template can be used for etching or for positioning brackets on teeth.

19 Claims, 20 Drawing Sheets

U.S. PATENT DOCUMENTS

| | | | |
|---|---|---|---|
| 4,656,860 A | 4/1987 | Orthuber et al. |
| 4,663,720 A | 5/1987 | Duret et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,837,732 A | 6/1989 | Brandestini et al. |
| 4,850,864 A | 7/1989 | Diamond |
| 4,856,991 A | 8/1989 | Breads et al. |
| 4,936,862 A | 6/1990 | Walker et al. |
| 4,937,928 A | 7/1990 | Van Der Zel |
| 4,964,770 A | 10/1990 | Steinbichler et al. |
| 4,975,052 A | 12/1990 | Spencer et al. |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,486 A | 9/1995 | Andersson et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,518,397 A | 5/1996 | Andreiko et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Andersson et al. |
| 5,605,459 A | 2/1997 | Kuroda et al. |
| 5,607,305 A | 3/1997 | Andersson et al. |
| 5,645,421 A | 7/1997 | Slootsky |
| 5,655,653 A | 8/1997 | Chester |
| 5,683,243 A | 11/1997 | Andreiko et al. |
| 5,733,126 A | 3/1998 | Andersson et al. |
| 5,740,267 A | 4/1998 | Echerer et al. |
| 5,791,896 A | 8/1998 | Ipenburg |
| 5,971,754 A | 10/1999 | Sondhi et al. |
| 5,975,893 A | 11/1999 | Chishti et al. |
| 6,554,613 B1 | 4/2003 | Sachdeva et al. |
| 6,905,337 B1 | 6/2005 | Sachdeva |
| 6,918,761 B2 | 7/2005 | Sachdeva |
| 7,137,812 B2 | 11/2006 | Cleary et al. |
| 7,252,509 B2 | 8/2007 | Sachdeva |
| 2003/0027098 A1 | 2/2003 | Manemann et al. |
| 2003/0194677 A1 | 10/2003 | Sachdeva et al. |
| 2003/0224316 A1 | 12/2003 | Marshall |
| 2004/0175670 A1 | 9/2004 | Kopelman et al. |
| 2005/0208450 A1 | 9/2005 | Sachdeva et al. |

FOREIGN PATENT DOCUMENTS

| | | |
|---|---|---|
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis,"AADR Abstract #607, 1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, 112-123.

Baumrind et al., Mapping the Skull in 3-D, Reprinted from The Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research*; vol. 67, Special Issue Mar. 9-13, 1988, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion In The Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7, Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner" *Am. J. Orthod.*, vol. 55, No. 1, (Jan. 1969), pp. 23-31.

Crawford, "Computers in Dentistry: Part 1: CAD/CAM: The Computer Moves Chairside," "Part 2: F. Duret—A Man With A Vision," "Part 3: The Computer Gives New Vision-Literally," "Part 4: Bytes 'N Bites" The Computer Moves From The Front Desk To The Operatory, *Canadian Dental Journal*, vol. 54(9), (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1980) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastics and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

DeFranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13, (1990).

Duret et al, "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisae," (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, vol. 36, No. 5, (May 1950) pp. 368-374.

Faber et al., "Computerized Interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery," Abstract of Papers, *Journal of Dental Research*, vol. 70 (1987), pp. 754-760.

Gim-Alldent Deutschland, "Das DUX System: Die Technik" 2 pages total, (1990).

Grayson, "New Methods for Three Dimensional Analysis of Craniofacial Deformity," Symposium: Computerized Facial Imaging in Oral and Maxiofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery," *JCO*, (Apr. 1989), pp. 262-328.

Heaven et al., "Computer-based Image Analysis of Artificial Root Surface Caries," Abstracts of Papers, *Journal of Dental Research*, vol. 70, Apr. 17-21, 1991, p. 528.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

JCO Interviews, "Craig Andreiko, DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16, 1989, pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.*, vol. 63, No. 11 (Nov. 1984), pp. 1298-1301.

Kesling, "Coordinating the Predetermined Pattern and Tooth Positioner With Conventional Treatment" *Am. J. Orthod. Oral. Surg.*, 32:285-293, 1946.

Kesling, "The Philosophy of the Tooth Positioning Appliance" *Am. J. Orthod. Oral. Surg.*, 31(6):297-304, 1945.

Kleemann et al., "The Speed Positioner" *J. Clin Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop.* 44, 370-376 (Nr. 5), 1983.

McCann, Inside the ADA, *Journal Of The American Dental Assoc.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro, " *Schwizerische Monatsshrift fur Zehnmedizin*, vol. 85 (1985), p. 1118-1129.

Nahoum, "The Vacuum Formed Dental Contour Appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama et al., "A New Construction Of Tooth Repositioner By LTV Vinyl Silicone Rubber" J. Nihon University School of Dentistry, 19(2):93-102, 1977.

Pinkham, "'Foolish' Concept Propels Technology," *Dentist*, Jan./Feb. 1989, 3 pages total.

Pinkham, "Inventor's CAD/CAM May Transform Dentistry," *Dentist*, Sep. 1990, 3 pages total.

Ponitz, "Invisible Retainers", *Am. J. Orthodontics*, vol. 59, No. 3, Mar. 1971, pp. 266-272.

Procera Research Projects, *PROCERA Research Projects 1993—Abstract Collection*, 1993, pp. 3-24.

Rekow, "A Review of the Developments in Dental CAD/CAM Systems," (contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?"*Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1988) pp. 53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: Arch Form, A review of the literature," *European Journal of Orthodontics*, vol. 3, No. 4 (1981), pp. 279-284.

Sakuda et al., "Integrated Information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Shilliday, "Minimizing Finishing Problems With the Mini-Positioner" *Am. J. Orthod.* 59:596-599, 1971.

Siemens, "CEREC—Computer-Reconstruction, "High Tech in der Zahnmedizin, 14 page total, (1990).

Sirona Dental Systems GmbH, CEREC 3D, Manuel utilisateur, Version 2.OX (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Provisional Patent Application No. 60/050,342, filed Jun. 20, 1997, 41 pages total.

Van Der Linden et al., "Three-Dimensional Analysis of Dental Casts by Means of the Optocom," *J Dent Res*, Jul./Aug. 1972, vol. 51, No. 4, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Várady et al., Reverse Engineering Of Geometric Models—An Introduction. Computer-Aided Design, 29 (4):255-268, 1997.

Warunek et al., "Clinical Use Of Silicone Elastomer Appliances" *JCO*, MH (10):694-700, 1989.

Warunek et al., "Physical And Mechanical Properties of Elastomers In Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis of Three-Dimensional Tooth Movement in Orthodontics," *Frontiers in Med. and Biol. Eng'g*, vol. 1, No. 2 (1988), pp. 119-130.

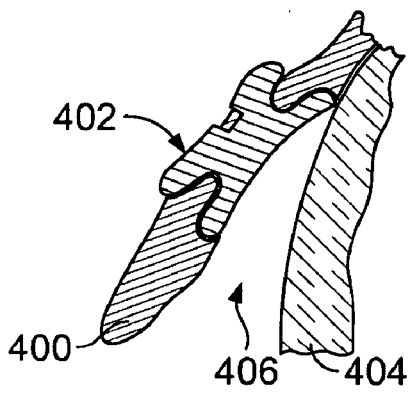
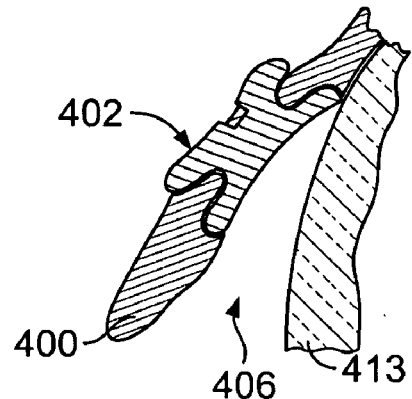
FIG. 6A    FIG. 6B
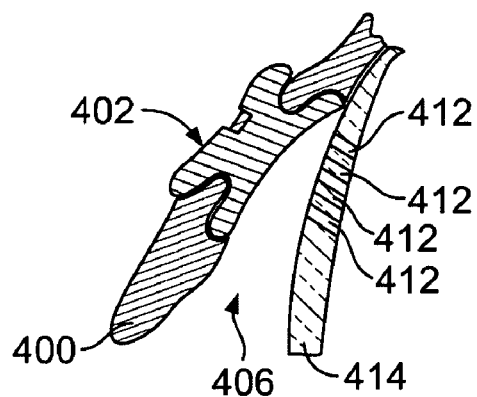
FIG. 6C
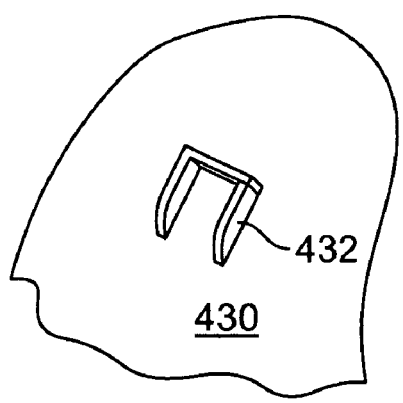
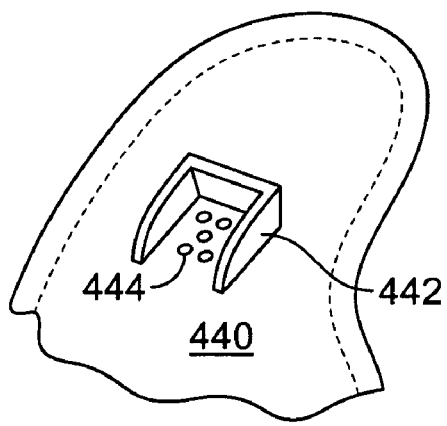
FIG. 7A    FIG. 7B

SYSTEMS AND METHODS FOR FABRICATING A DENTAL TEMPLATE WITH A 3-D OBJECT PLACEMENT

BACKGROUND

This application is a continuation-in-part of U.S. patent application Ser. No. 10/375,223, filed Feb. 26, 2003 and now abandoned.

The present invention relates generally to the field of orthodontics.

One objective in orthodontics is to move a patient's teeth to a position where the teeth function optimally and are also aesthetically pleasing. Conventional appliances such as braces and wires can be positioned on a patient's teeth by a treatment provider such as an orthodontist or a suitably trained dentist. Once mounted on the teeth, the hardware exerts continual forces on the teeth and gradually urges the teeth toward their ideal positions. Over a period of time, the treatment provider adjusts the braces and the wires to move the teeth toward their final destination.

Orthodontic brackets are often bonded directly to the patient's teeth. Typically, a small quantity of adhesive is placed on the base of each bracket and the bracket is then placed on a selected tooth. Before the adhesive is set, the bracket is maneuvered to a desired location on the tooth. Once the adhesive has hardened, the bracket is bonded to the tooth with sufficient strength to withstand subsequent orthodontic forces as treatment progresses. One shortcoming with this technique is the difficulty in accessing the optimal surface for bracket placement on severely crowded teeth or in teeth where the bonding surface is obstructed by teeth in the opposing arch during jaw closure. With posterior teeth, the treatment provider may have difficulty seeing the precise position of the bracket relative to the tooth surface. The amount of time needed to carry out the bonding procedure may be a nuisance both to the patient as well as to the treatment provider. Also, the necessity of minimizing moisture contamination from the patient's saliva can prolong the procedure and also unduly impair the accuracy of placement of the brackets on the teeth. All of these factors increase the chance that the ultimate adhesive bond will not have sufficient strength to retain the brackets on the teeth during treatment. One way to overcome some of the limitations of direct bracket placement is with indirect bonding. Typically, an impression of each of the patient's dental arches is taken and a replica plaster or "stone" model is made from each impression and sealed. Brackets are bonded to the sealed stone models using a temporary cement. A transfer tray is then made by placing matrix material over both the model and the brackets on the model. For example, a heated plastic sheet matrix material may be placed over the model and brackets and then under pressure. The plastic sheet material then assumes a configuration that precisely matches the shape of the replica teeth of the stone model with the brackets in the desired position. The plastic material is then allowed to cool and harden to form a tray. The temporary adhesive is removed, and permanent adhesive is placed on the base of each bracket in the tray, and the tray with the embedded brackets then placed over matching portions of the patient's dental arches. Since the configuration of the interior surface of the tray closely matches the respective portions of the patient's dental arches, each bracket is ultimately positioned on the patient's teeth at precisely the same location that corresponds to the previous location of the same bracket on the stone model. The adhesive is hardened and the matrix material removed, leaving the brackets in the desired positions. This method however, is labor intensive. An additional problem with the indirect method is that brackets may become dislodged during the removal of the matrix from the dental arches. The problem of proper access to tooth surfaces for optimal placement in the event of severely crooked teeth or teeth which interfere with the opposing arch such that brackets cannot be placed is also not addressed.

New methods such as those described in U.S. Pat. No. 5,975,893, commonly assigned to the assignee of the instant invention, allow the treatment to be planned in advance and a plurality of polymeric shell appliances are fabricated at the outset of treatment. The use of polymeric shell appliances provides treatments that are more comfortable; less visible, and removable by the patient, and greatly improves patient compliance, comfort, and satisfaction.

Since each patient is unique and requires customized treatment, on occasion, a patient may need to utilize a combination of braces/wires and shell appliances. Ideally, a device would enable precise placement of brackets on teeth with minimal risk of displacing the brackets upon removal of the matrix and allow final placement to be independent of adjacent geometries. In other words, placement of obscured tooth surfaces may be accomplished at a later time when the tooth surfaces have been exposed through initial uncrowding of severely overlapped teeth.

SUMMARY

A dental template is disclosed to support positioning an object on a patient's tooth oriented in such a way that all the objects as a whole are lined up to a user defined ideal arrangement. Also, a method is disclosed for fabricating the template. The method includes digitizing the patient's teeth; adding virtual objects to predetermined locations on the digitized teeth; and fabricating the dental template to locate the object on the patient's teeth. The dental template is designed to locate each object at a predetermined inclination or a predetermined angulation on the patient's tooth. The template can be used for etching or for positioning brackets on teeth.

Advantages of the template may include one or more of the following. The methods, steps, and algorithms described above that are used to form the requisite digital representation of an orthodontic template. Additional features, bodies, or component data files can be used in addition to the tooth files used to form said template. The elements, or concepts of the creation methods described above can be mixed or matched. That is, a file may also be created by using some steps from one method and other steps from one or more other methods.

The template allows standardized brackets to be accurately positioned on teeth regardless of tooth surface variations from the norm that the bracket base is designed for. The treatment can be done virtually and the placement of the brackets can be done using a template device that is a removable guide. This device allows precise placement of the bracket and enables bracket placement onto specific teeth independent of overall arch geometry. The template makes it easier for a less well-trained or an untrained person to bond a bracket. The system minimizes variations in the perception of distance and angles. The template provides a very precise control on the placement of the bracket. Since bracket placement is one of the critical variables to successful treatment, the template improves treatment precision from patient to patient and from tooth to tooth.

The device itself may not necessarily contain the bracket as with traditional indirect bonding (IDB) templates, but rather, directs the user as to the precise location where the bracket should be placed based on geometric fit.

BRIEF DESCRIPTION OF THE DRAWINGS

FIGS. 6A-6C show one embodiment that enables controlled placement of the bracket base on a tooth.

FIGS. 7A-7B show other embodiments to position the orthodontic object to the tooth with a desired angulation and/or inclination.

DESCRIPTION

Figure 1:
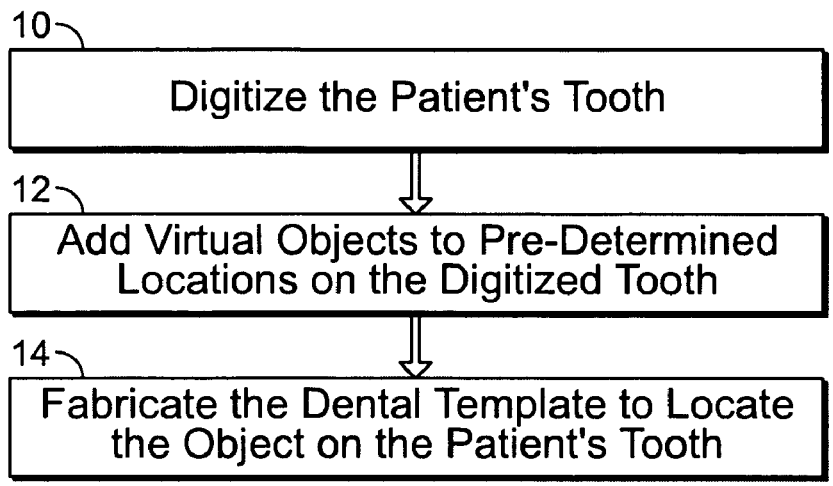
FIG. 1 shows an exemplary method or process to fabricate a dental template to position an object on a patient's tooth.

FIG. 1 shows an exemplary method or process to fabricate a dental template to position an object on a patient's tooth. First, the process digitizes the patient's tooth (10). Next, virtual objects are added to pre-determined locations on the digitized tooth (12). Finally, the process fabricates the dental template to locate the object on the patient's tooth (14). One detailed implementation of FIG. 1 is described in FIGS. 3A and 3B below.

Figure 2A:
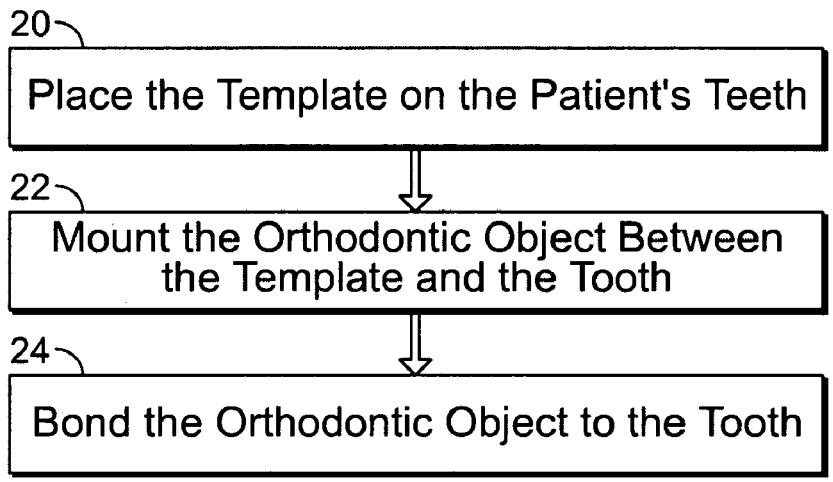
FIG. 2A shows an exemplary method or process for placing an orthodontic object on a patient's tooth.

FIG. 2A shows an exemplary method or process for placing an orthodontic object on a patient's tooth. The process uses the template fabricated in the process of FIG. 1. The process includes placing the template on the patient's teeth (20); mounting the orthodontic object between the template and the tooth (22); and bonding the orthodontic object to the tooth (24). In the bonding operation, chemical curing or light curing adhesives can be used. In chemical curing, separately supplied curing components are mixed together and a small quantity of the mixture is placed on the back of the bracket prior to placing the bracket on the tooth. Light-curable adhesives include a photo-initiator that initiates the curing reaction once the adhesive is exposed to a sufficient amount of light. A common method of using light-curable adhesives for direct bonding includes the steps of placing a small quantity of the adhesive on the base of the bracket and then placing the bracket on the patient's tooth. The practitioner then shifts the bracket on the tooth as may be needed. Once the bracket is in its precise, intended location, light from a dental curing unit is directed toward the adhesive for a time period sufficient to satisfactorily cure the adhesive.

Figure 2B:
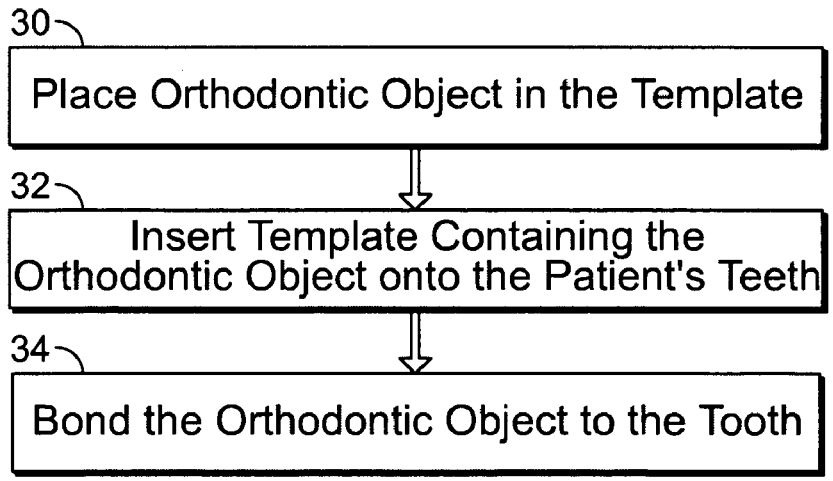
FIG. 2B shows a second method of placing the orthodontic object on a patient's tooth.

FIG. 2B shows a second method of placing the orthodontic object on a patient's tooth. In this process, the orthodontic object is placed in the template (30). Next, the process includes inserting the template containing the orthodontic object onto the patient's teeth (32). Finally, the process includes bonding the orthodontic object to the tooth (34).

Figure 3A:
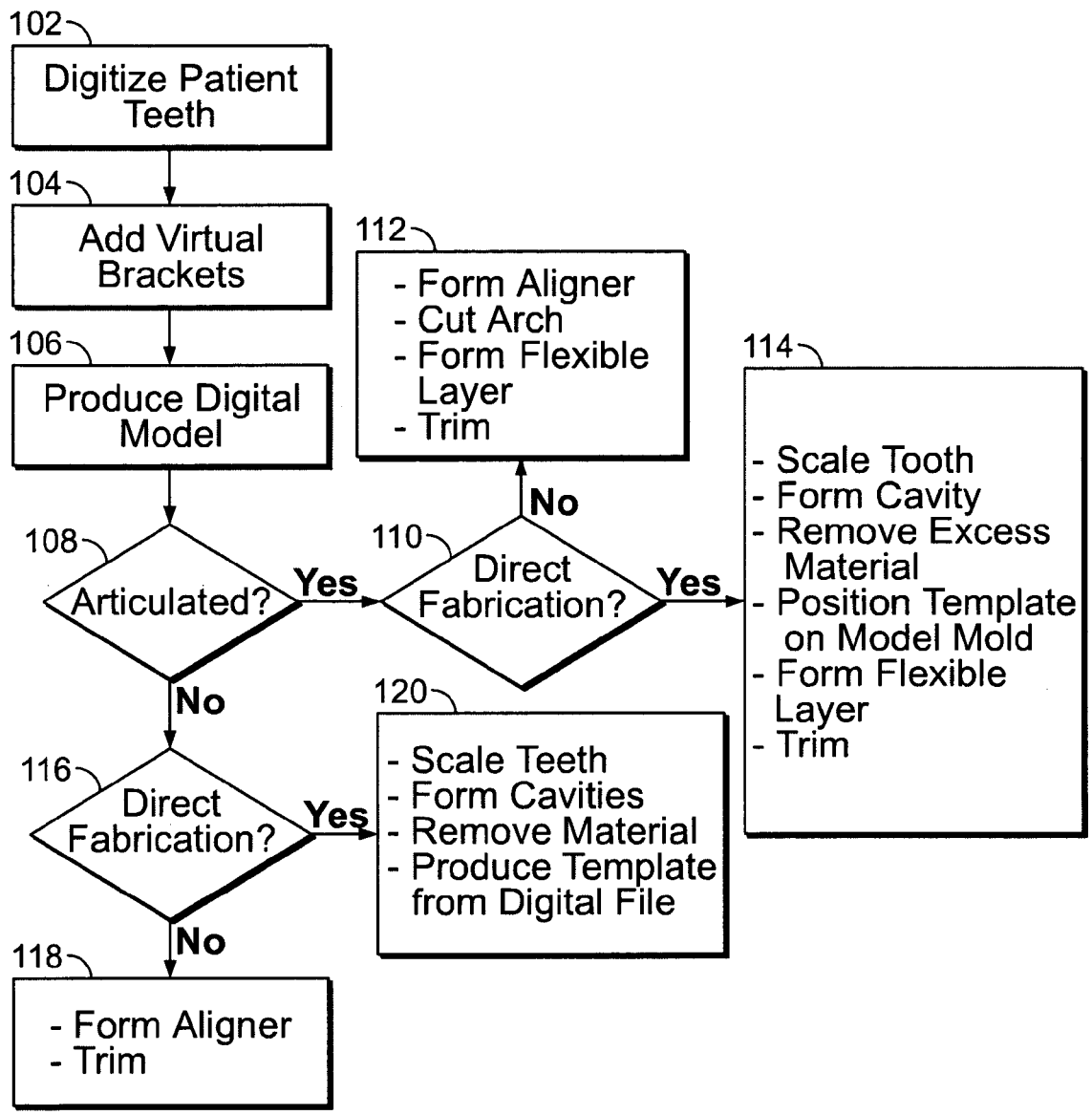
FIG. 3A illustrates an exemplary process for fabricating the dental template.

FIG. 3A illustrates an exemplary process for fabricating the dental template. First, a digital model of a patient's teeth of a patient is obtained (102). The digital model can be obtained in a variety of ways. For example, the patient's teeth may be scanned or imaged using well known technology, such as X-rays, three-dimensional x-rays, computer-aided tomographic images or data sets, magnetic resonance images, etc. There are a variety of range acquisition systems, generally categorized by whether the process of acquisition requires contact with the three dimensional object. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry).

Next, virtual brackets are selected (104). The virtual brackets are 3D models of existing brackets. The 3D models may be a computer aided design (CAD) model or may be scanned using scanners described above. The brackets may be positioned on a digitized tooth using a computer or workstation having a suitable graphical user interface (GUI) and software appropriate for viewing and modifying the images. The above-described component identification and component manipulation software is designed to operate at sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intra-oral physiology and teeth-moving dynamics, can simply use the component identification and manipulation software as a tool and disable or otherwise ignore the advice.

While the methods will rely on computer manipulation of digital data, the dental templates or appliance may be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare the template using pressure and vacuum molding techniques. While such manual creation of the appliance systems of the present invention will generally be much less preferred, systems so produced will come within the scope of the present invention.

Using the CAD workstation, a combined digital model of the virtual brackets and the teeth is produced (106).

In one implementation, one of four template embodiments can be selected: Direct-Articulated, Indirect-Articulated, Direct-Unified, and Indirect-Unified, as discussed in more detail in FIG. 3B.

Once the template has been fabricated, in one embodiment, the system sets the template over the model of the patient's arches or otherwise positions the template in the approximate locations of their respective teeth. A thermoformed, cast, or otherwise formed layer of flexible material is deposited on the bodies. The layer makes intimate and relatively durable contact with the bodies of the templates. This may be accomplished, among other ways, by adding or subtracting geometries to the bodies to engage well with the material layer. This method could be performed either by a factory or in the orthodontist's office.

The system produces both the template bodies and the inter-tooth portion(s) at the same time and subsequently alter the stiffness of the various parts. One way of achieving this would be to produce the entire arch with a 3-D printer, mask the tooth bodies from the inter-tooth portions, and embed the tooth bodies with a rigidifying agent and the inter-tooth portions with an agent to create flexibility.

From 108, if an articulated template is to be produced, the process proceeds to 110 where, if a directly formed template is produced, the process proceeds to 114 where each tooth is scaled; a cavity is formed to enclose the tooth when the dental template or appliance is inserted over the patient's teeth. Next, unnecessary structures are removed from the digital model. The digital model is produced as a physical model. A flexible pliable layer is formed and the resulting combination is trimmed to allow proper fit and function.

Alternatively, from 110, if indirect forming is to be done, the process forms an aligner, and cuts and removes excess material (112).

From 108, if a non-articulated template is to be indirectly-fabricated (116), an Aligner is formed and trimmed (118). In the case of a directly formed non-articulated template (116), the process proceeds to 120 where each tooth in the arch is scaled; cavities are formed to enclose the teeth when the dental template or appliance is inserted over the patient's teeth. Next, unnecessary structures are removed from the digital model. The digital model is produced as a physical model.

Figure 3B:
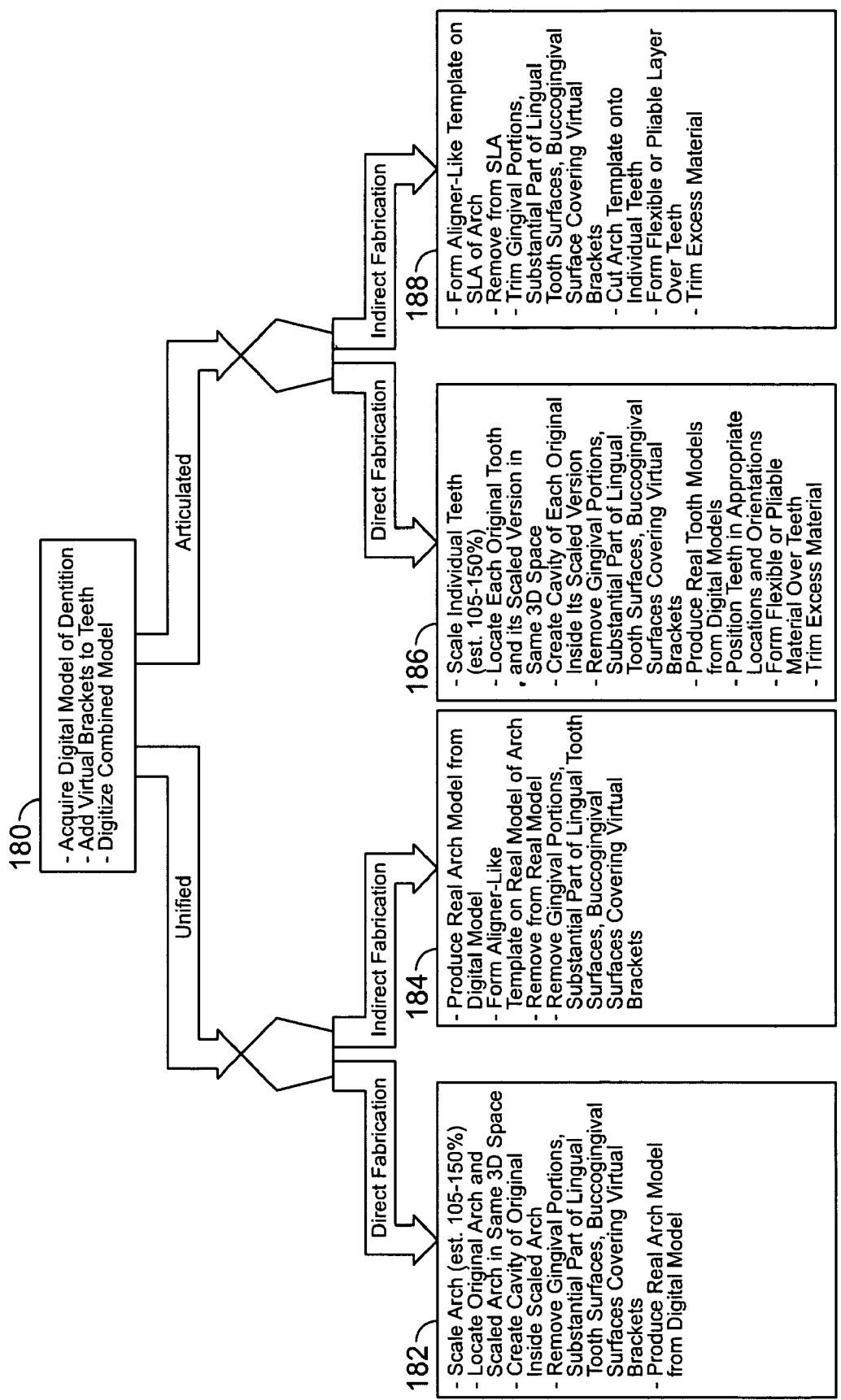
FIG. 3B shows a process for providing four possible templates.

FIG. 3B shows a process for providing four possible templates. First, the process acquires a digital model of dentition, adds virtual brackets to teeth, and creates a combined model (180). Next, one of four templates options can be selected. The first option is unified (or single piece)—direct fabrication option where the process scales the arch (est. 105-150%), locates original arch and scaled arch in same 3D space, creates cavity of original inside scaled arch, removes gingival portions, substantial part of lingual tooth surfaces, buccogingival surfaces covering virtual brackets, and produces real arch model from digital model (182).

In the second option (unified indirect fabrication), the process produces real arch model from digital model and forms a removable appliance (aligner) template on real model of arch. The template is removed from the real model, and the process then removes gingival portions, substantial part of lingual tooth surfaces, buccogingival surfaces covering virtual brackets (184).

In the third option (articulated direct fabrication), the process scales individual tooth (est. 105-150%), locates each original tooth and its scaled version in same 3D space, creates a cavity of each original inside its scaled version, removes gingival portions, substantial part of lingual tooth surfaces, buccogingival surfaces covering virtual brackets, produces real tooth models from digital models, positions teeth in appropriate locations and orientations, forms a flexible or pliable material over teeth, and trims excess material from the template (186).

In the fourth option (articulated indirect fabrication), the process forms an aligner-like template on a mold of an arch. The template is removed from the mold and gingival portions, substantial part of lingual tooth surfaces, and buccogingival surface covering virtual brackets are trimmed. The process cuts an arch template onto an individual tooth. A flexible or pliable layer is formed over the template, and excess material is trimmed (188).

In yet another embodiment, a process obtains tooth geometries. If direct fabrication is to be used, the process performs the following:
Scale the teeth to values likely within the range 105-150%.
Co-locate the original (100%) teeth and the scaled teeth in the same 3D space
Place a virtual bracket or other appropriate geometry at a specific location and in a specific orientation on each tooth to be treated.
Cavity the original teeth and the brackets in the scaled teeth.
Remove from the resulting template or body those aspects that would be below the gingival line. Remove the portions of the resultant body buccal and gingival to the brackets remove a substantial portion or all of the lingual aspect of the resultant body.
Convert this computer model to a real part, likely through the use of a rapid prototyping method (e.g. Fused Deposition Modeling, 3-D Printing, and stereolithography).

If indirect fabrication is to be done, the following operations are done using an arch model:
Form an Aligner-like appliance or template over an arch model that has brackets or other appropriate geometries properly located on the teeth.
Remove from the Aligner or template those aspects that would be below the gingival line or in direct interproximal contact with adjacent teeth. Remove the portions of the Aligner buccal and gingival to the bracket. Remove a substantial portion or all of the lingual aspect of the Aligner.

After completion, the process ships the templates, bodies or the completed appliance to the orthodontist either at the onset of treatment or when it is requested.

Figure 4A:
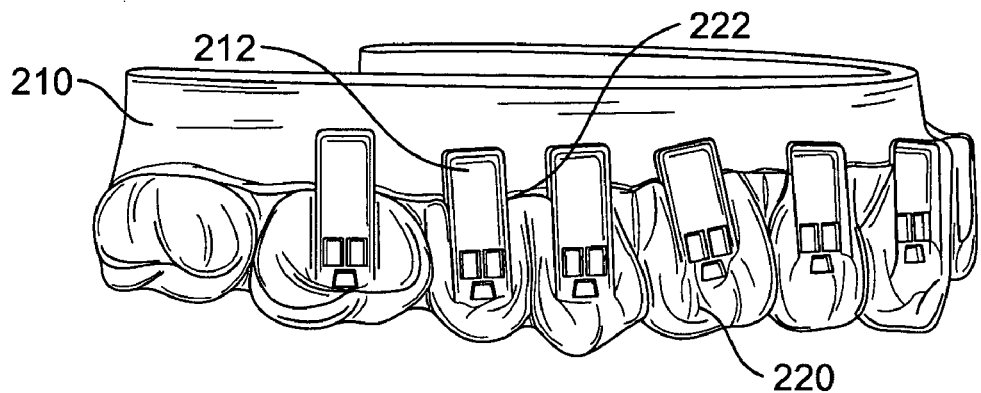
FIGS. 4A-4D show perspective views of various templates.

FIG. 4A shows one embodiment of a dental template 220 or appliance formed over a mold 210. The template looks like a removable appliance; however, it has openings 222 or "portholes" approximating the footprint, key portions of the footprint, and/or possibly other geometrical features of a bracket to guide the precise placement of the bracket on its respective tooth. The template 220 with the openings 222 or "portholes" may also be a guide for enamel etching or adhesive placement.

The mold 210 is a physical rendition of a digital model that has been fabricated using rapid prototyping methods. A bump or projection 212 rises from the mold 210 so when the dental template or appliance is thermal-formed, an opening 222 is formed on the template 220. The opening 222 is where the template is cut out along the edge of the bump or projection 212. The opening 222 has a bracket support edge 226, whose operation is described in more detail in FIG. 4B. In addition to the support edge 226, the template 220 may have features that will minimize the retention of it on the dental anatomy. For example, the lingual side of the device may not have maximum coverage.

Fabrication methods for the mold 210 employ a rapid prototyping device such as a stereolithography machine or a fused deposition modeling machine. A suitable rapid prototyping machine is Model SLA-250/50 available from 3D System, Valencia, Calif. The rapid prototyping machine selectively hardens a liquid or other non-hardened resin into a three-dimensional structure, which can be separated from the remaining non-hardened resin, washed, and used either directly as the appliance or indirectly as a mold for producing the appliance. The prototyping machine receives the individual digital data sets and produces one structure corresponding to each of the desired appliances. Generally, because the stereolithography machine may utilize a resin having non-optimum mechanical properties and which may not be generally acceptable for patient use, the prototyping machine produces the mold 210. After the positive model is prepared, a conventional pressure or vacuum molding machine may be used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine produces each of the appliances directly from the positive tooth model and the desired material. Suitable vacuum molding machines are available from Raintree Essix, Inc.

In one embodiment, the template is made from a thick material (for example 0.03 inches or more) to provide the user with more guidance in the depth direction. Furthermore, the thick template allows easier lining the bracket to the tooth.

More information on the fabrication of the dental template or appliance is disclosed in U.S. Pat. No. 6,499,997 "Manipulable dental model system for fabrication of a dental appliance"; U.S. Pat. No. 6,497,574 "Modified tooth positioning appliances and methods and systems for their manufacture"; U.S. Pat. No. 6,488,499 "Methods for correcting deviations in preplanned tooth rearrangements"; U.S. Pat. No. 6,485,298 "System and method for releasing tooth positioning appliances"; U.S. Pat. No. 6,471,511 "Defining tooth-moving appliances computationally"; U.S. Pat. No. 6,463,344 "Efficient data representation of teeth model"; U.S. Pat. No. 6,457,972 "System for determining final position of teeth"; U.S. Pat. No. 6,454,565 "Systems and methods for varying elastic modulus appliances"; U.S. Pat. No. 6,450,807 "System and method for positioning teeth"; U.S. Pat. No. 6,409,504 "Manipulating a digital dentition model to form models of individual dentition components"; U.S. Pat. No. 6,406,292 "System for determining final position of teeth"; U.S. Pat. No. 6,398,548 "Method and system for incrementally moving teeth"; U.S. Pat. No. 6,394,801 "Manipulable dental model system for fabrication of dental appliances"; U.S. Pat. No. 6,390,812 "System and method for releasing tooth positioning appliances"; U.S. Pat. No. 6,386,878 "Systems and methods for removing gingiva from teeth"; U.S. Pat. No. 6,386,864 "Stress indicators for tooth positioning appliances"; U.S. Pat. No. 6,371,761 "Flexible plane for separating teeth models"; U.S. Pat. No. 6,318,994 "Tooth path treatment plan"; U.S. Pat. No. 6,309,215 "Attachment devices and method for a dental appliance"; U.S. Pat. No. 6,299,440 "System and method for producing tooth movement"; U.S. Pat. No. 6,227,851 "Manipulable dental model system for fabrication of a dental appliance"; U.S. Pat. No. 6,227,850 "Teeth viewing system"; U.S. Pat. No. 6,217,325 "Method and system for incrementally moving teeth"; U.S. Pat. No. 6,210,162 "Creating a positive mold of a patient's dentition for use in forming an orthodontic appliance"; and U.S. Pat. No. 5,975,893 "Method and system for incrementally moving teeth," the contents of which are hereby incorporated by reference.

Figure 4B:
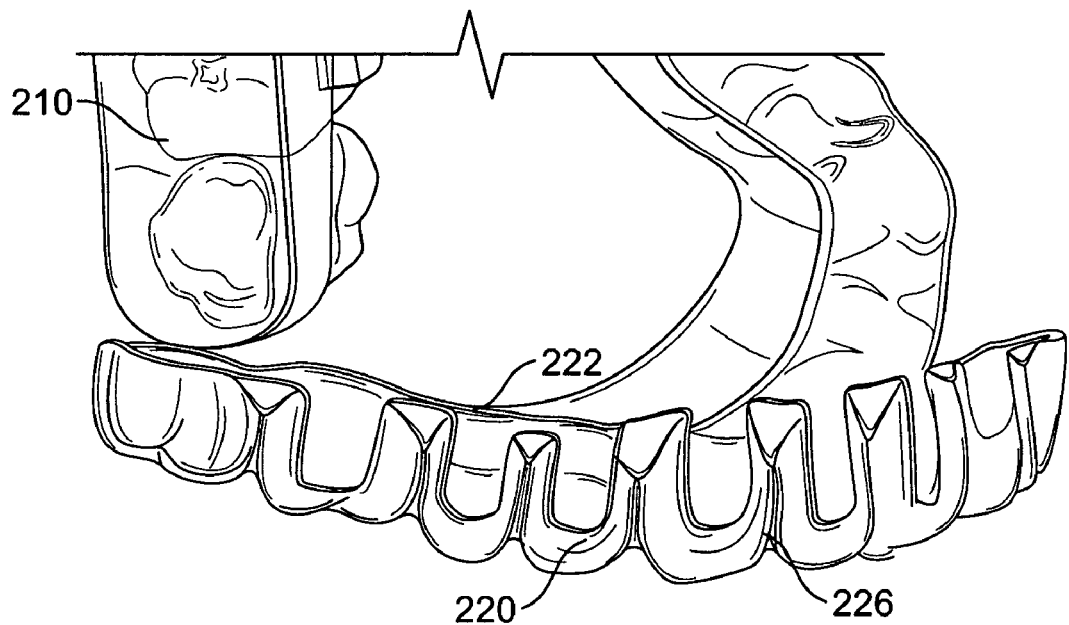

Turning now to FIG. 4B, the template 220 is separated from the mold 210. The opening 222 allows a bracket base to fit into the opening 222. Bracket support edge 226 is needed to securely position the bracket in the template 220. In this embodiment, the bracket support edge 226 is curvaceous. If the edge 226 had been terminated as a simple flat edge, the bracket can be located in X and Y surfaces on the tooth, but the Z direction (buccal lingual direction) would not be controlled. The edge 226 provides the needed control of the bracket's degree of freedom in the Z direction to allow orientation of the bracket about any given axis. Those features allow the bracket to be secured in the proper position and orientation on its respective tooth. The edge 226 can change, depending on vendor-to-vendor or prescription-to-prescription.

Another embodiment of the template can be used for etching bonding chemicals on the patient's teeth. The etching template directs the user to predetermined locations on the teeth surfaces that need to be bonded. The etching template can be either the format of a windowed template or a concave surfaced template where bonding gel is loaded or pre-loaded into the concavity.

Figure 4C:
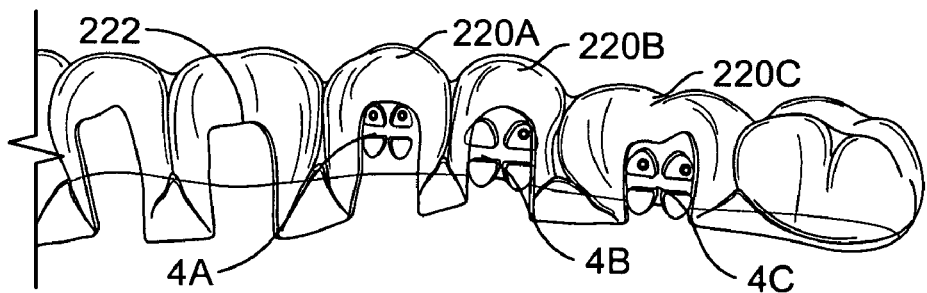

FIG. 4C shows a template wherein each of the openings, cut-outs, port-holes, or slots 222 in the template 220 are designed to fit particular brackets 4A, 4B and 4C, each of which fits into its respective portion on the template.

Figure 4D:
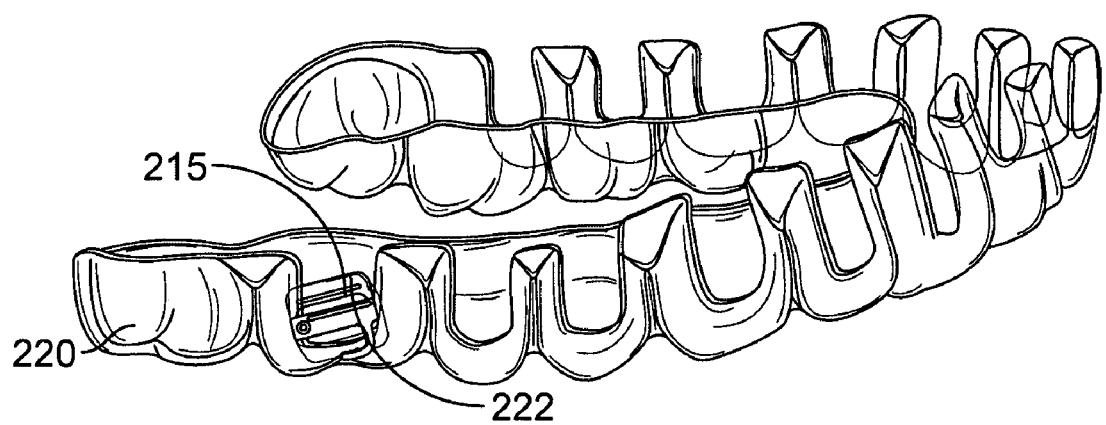

FIG. 4D shows that the system is not limited to bracket design or shape. In FIG. 4D, a molar tube bracket 215 can be placed on the opening 222. Hence, the template 220 is not limited to any specific bracket. Rather, any form of fixed orthodontic appliances placed on a tooth could be accommodated.

Figure 5A:
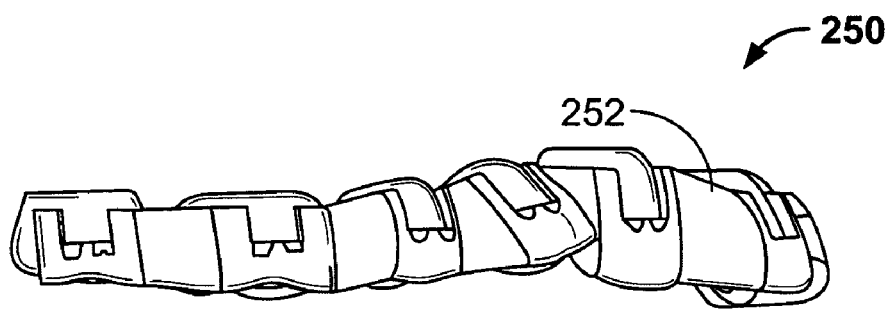
FIGS. 5A and 5B illustrate two embodiments of articulated templates.
Figure 5B:
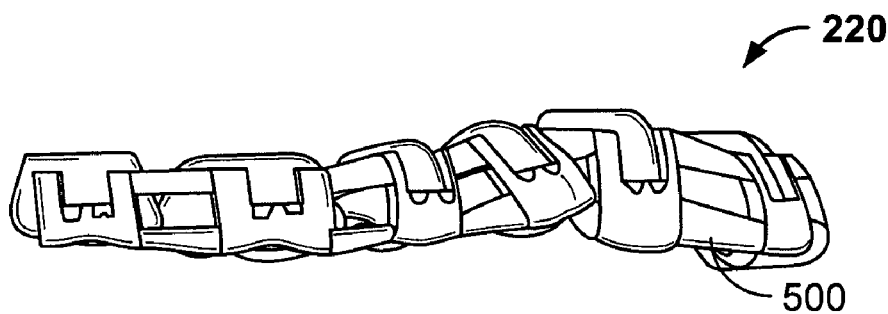

FIGS. 5A and 5B illustrate two exemplary embodiments of articulated templates. FIG. 5A shows two segments joined at the interproximal regions of two adjacent teeth. A number of alternate methods to join the teeth can be used, including that the joining methods could be alternate or vary from one interproximal region to the next. Further, the joining method could also be a layer or layers that cover additional or different surfaces of the teeth as depicted in FIG. 5B.

In FIG. 5A, the template is made up of a number of movable template components 250. Each of the template components 250 can be mounted on a patient's tooth to facilitate bracket bonding. The movable template components 250 are physically linked together by a sheet of material 252 deposited above the components 250 so that they do not break-up or otherwise become disassembled upon removal from its mold or stereolithography apparatus (SLA) model. The articulated templates are advantageous in that they provide greater adjustment flexibility.

The template can additionally be used as an etching template. An etching template allows the doctor to precisely etch the areas of the teeth on which the brackets will be placed. The small windows bound the regions that will be etched to minimize teeth sensitivity to etching or unwanted enamel removal. In another version of the etching template, the cut outs would not be formed. Instead those areas would be concavities facing the tooth surfaces. These concavities would contain an etching compound. The user would expose or activate the etching compound prior to setting the template on the teeth.

The template 220 may be made from materials that contain physical property switches for ease of removal. These switches might include temperature responsive, pH responsive, moisture responsive or a multi-layer system wherein the layers have varying physical properties. The section 500 (FIG. 5B) represents a flexible or pliable material. Additionally, the material could be fiber, cord, fiber mesh, or a fiber-reinforced solid. The interproximal material can be homogenous or heterogeneous.

Orthodontic brackets are designed and produced with a fixed base profile for a given manufacturer prescription, and usage. The bracket base is that surface that is the interface with the tooth. Since a patient's tooth morphologies are unique, the bracket base and its underlying tooth may not mate well. Typically, a gap exists between the bracket base and the tooth surface. This gap needs to be filled to form a "Custom Base". The custom base may involve adjusting the angulation and/or inclination of the bracket base when it is applied to the tooth.

FIGS. 6A-6C show another embodiment that enables controlled placement of the bracket base on a tooth 404. FIG. 6A shows the template 400 over the tooth 404, while FIG. 6B shows the template 400 over a model 413. The template 400 contains a bracket 402. A gap 406 exists between the tooth 404 and the template 400 In FIG. 6B, the gap 406 exists between bracket and model. The bracket is located in its preferred position with a predetermined torque (inclination) and a predetermined tip (angulation). FIG. 6C shows the template on a shelled model which has through holes so the gap may be filled from within the model 414. A suitable epoxy is applied to fill the gap.

The bonding template can spatially fix the bracket while still leaving access to the gap 406. The template can be applied to an actual tooth or a model of the tooth. This access could be through the appropriate geometry in the template with or without an applicator designed for the purpose.

In the case of using the model of tooth, the model could be a shell that has hole(s) 412 to access the back of the bracket 402. Also, the customized base could be formed by pressing one model into another while the bracket is spatially fixed by the template 400. In this case, the outer 'model' would be a structure similar to the template, but more rigid and covers more of the teeth's surfaces. The inner 'model' would represent the actual teeth. The base gap would have been first filled with a bonding medium (e.g. adhesive). When the two models are fit together, the bonding medium is compacted into the gap and any excess flash around the bracket is removed. Yet another method would have a hollow model to represent the teeth, a template over this to fix the brackets in space, and a second model that nests in the first hollow model. When this latter is pressed into the hollow model, adhesive is forced through holes in the hollow model that are located behind the brackets' bases. After curing the adhesive, the two models are removed so the brackets and their custom bases remain in the template.

The template with the pre-specified or predetermined inclination or angulation is designed as follows. First, the system digitizes the patient's tooth. Next, an operator uses a dental CAD system to add a virtual object to a predetermined location on the digitized tooth. The CAD system is used to move the virtual object to a predetermined inclination or a predetermined angulation above the tooth. The resulting data is sent to a fabrication machine to fabricate the dental template to specifically locate the object on the patient's tooth with the determined inclination and/or angulation.

During use, a dental professional mounts the orthodontic object or bracket on the template and places the template on the patient's teeth or a model thereof. Since the template holds the bracket at the pre-specified angulation and/or inclination, the base of the bracket is accurately positioned above the tooth. The dental professional injects epoxy into the gap between the bracket and the tooth to bond the orthodontic object to the tooth with the desired angulation and/or inclination.

FIGS. 7A-7B show other embodiments to position the orthodontic object to the tooth with the desired angulation and/or inclination. In the embodiment of FIG. 7A, a plurality of rails 432 is formed on a tooth model 430. In the embodiment of FIG. 7B, rails 442 are also positioned on a tooth model 440. A plurality of openings 444 is provided on the model 440 to allow access to the base of a bracket that seats on or in the rails. The rails 432 and 442 are designed to provide proper angulation and/or inclination of the brackets on the tooth in addition to the proper locus.

In one embodiment, two or more rails or ridges are created along outside edges of a bracket on a suitable model substrate. The substrate can be Plaster, Resin, or Polymer substrate. A bonding medium is applied over the vicinity of the base. The bonding medium or epoxy may flow beyond the dimensions of the base. The bracket is then pressed against the rails or into channels in the rails which conform to the bracket base to force the correct spatial positioning and also limit it to the correct facial position. The rails also limit the base of the bracket to the correct facial position. The bonding medium is then cured. The bracket and custom base are removed from the substrate, which preferentially does not support or allow for a resilient bond to the adhesive.

Figure 8:
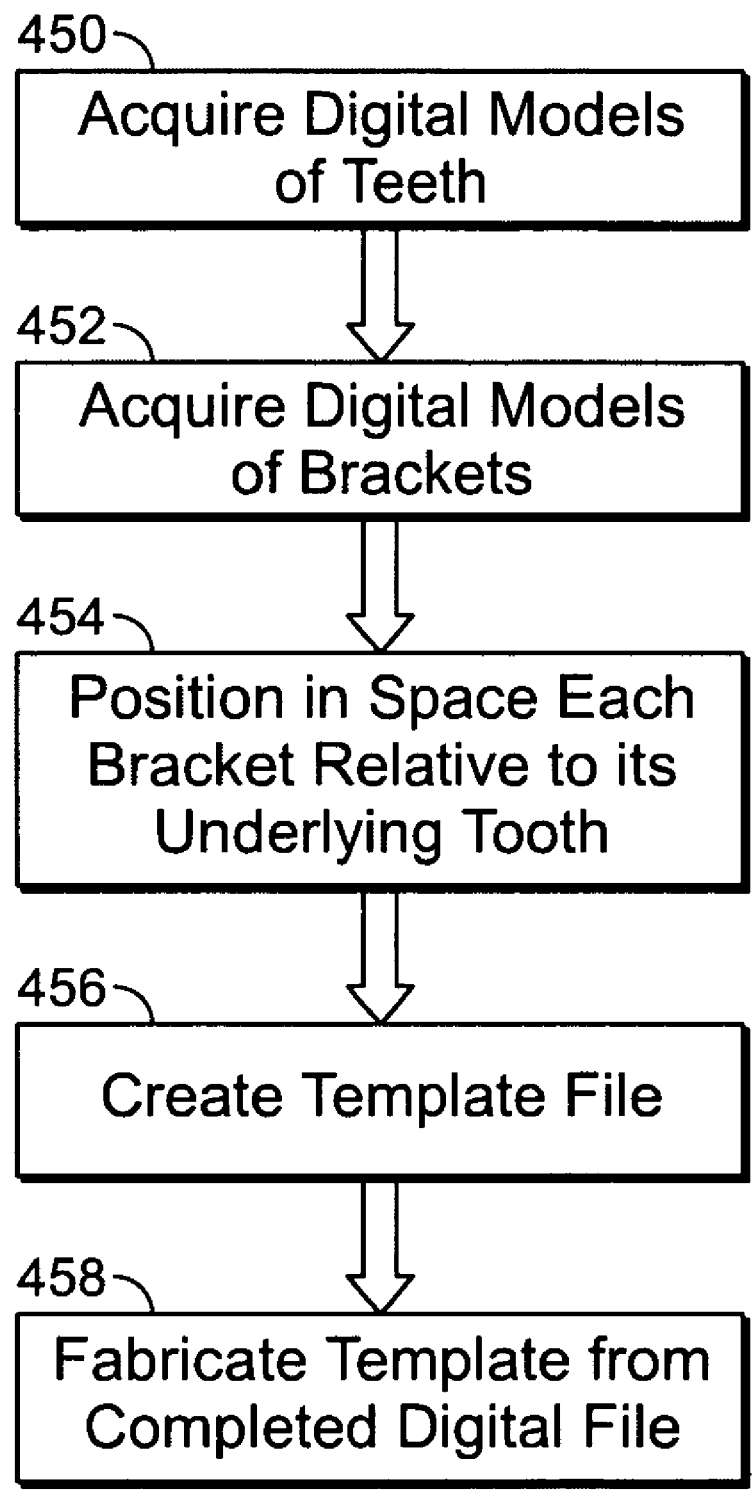
FIG. 8 is an exemplary flow-chart of a process to position the orthodontic object in an arbitrary 3D position with predetermined angulation and/or inclination.

Turning now to FIG. 8, an exemplary process to form a template that can position a bracket in any arbitrary three-dimensional position is shown. First, the process acquires a digital model of teeth (450). Next, the process acquires digital models of brackets to be supported by the template (452). Next, the process positions in 3D space each bracket relative to its underlying tooth (454). Methods of determining these positions include: Andrews' Straight Wire, Roth, MBT, measuring the distance and angles between bracket geometries and biological referents, or based on doctors' specific theories or philosophies. The process then creates a template file as disclosed herein (456). The template is fabricated from the completed digital file 458.

Figure 9:
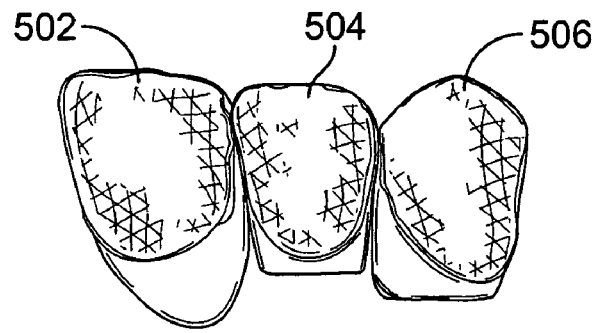
FIGS. 9-41 show various embodiments of digitally defining and forming dental templates.
Figure 10:
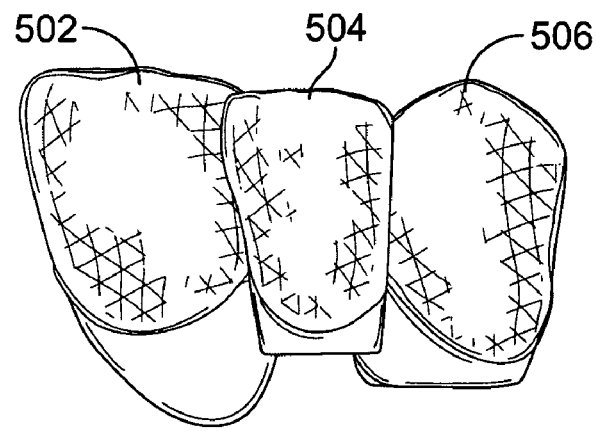
Figure 11:
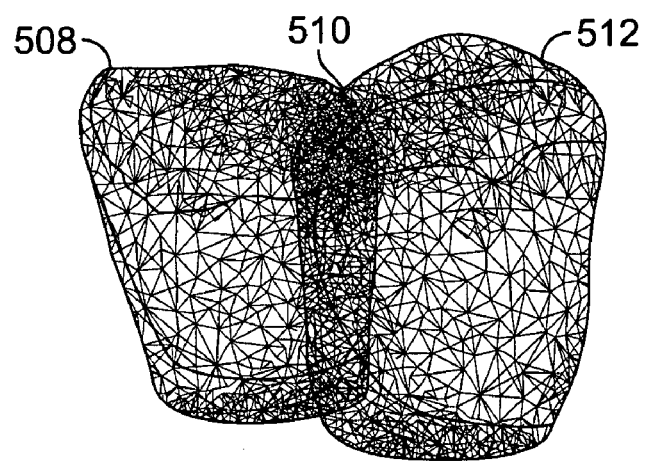
Figure 12:
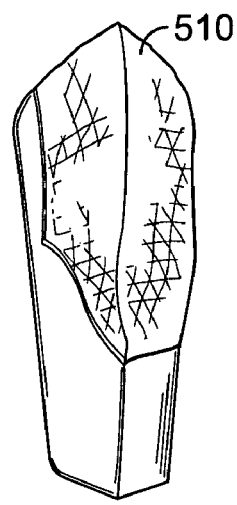

FIG. 9 illustrates a presentation of three scanned or otherwise captured digital models or representations of human teeth 502, 504 and 506, at 100% scale. FIG. 10 illustrates scaled tooth models from those of FIG. 9. In this embodiment, the scaling factor is 140%, but the scaling can be between approximately 105% and 150%. FIG. 11 shows where the tooth models 508 and 512 overlap. A wire frame representation is used to show a common volume 510. This common volume identifies bodies that may conflict with creating a suitable template. FIG. 12 shows a solid representation of a septa 510.

Figure 13:
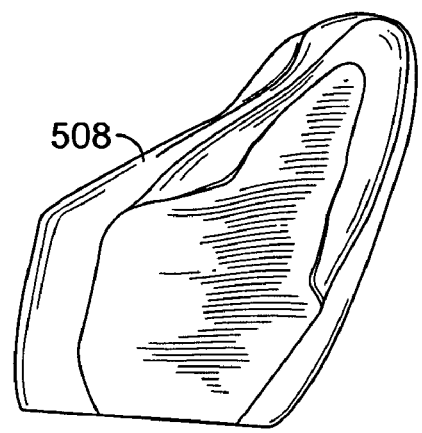
Figure 14:
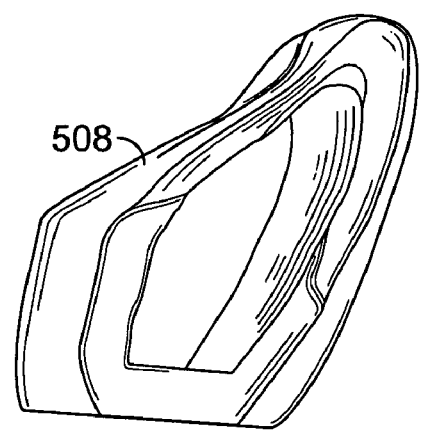

FIGS. 13 and 14 show a scaled tooth model 508, in this case the tooth model 508 is scaled up 140%. FIG. 13 shows a removal from the near side (side closest to viewer) of the model of the common volume 510 shared between the tooth model 508 and its adjacent tooth model 512. FIG. 14 shows the tooth model 508 with the common volume 510 removed from the near surface of the tooth and with the 100% tooth model subtracted from the tooth model 508. FIG. 14 thus is a shell that covers the 100% tooth model.

Figure 15:
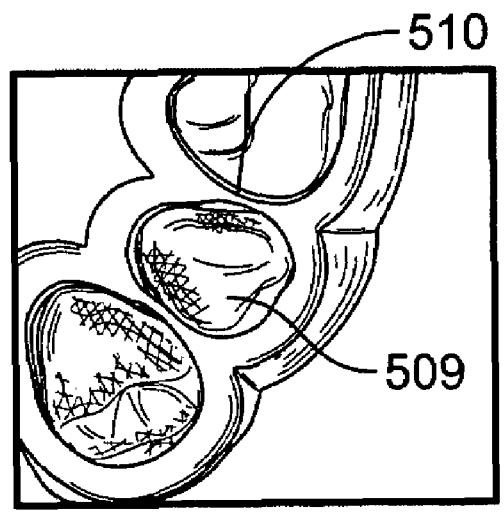
Figure 16:
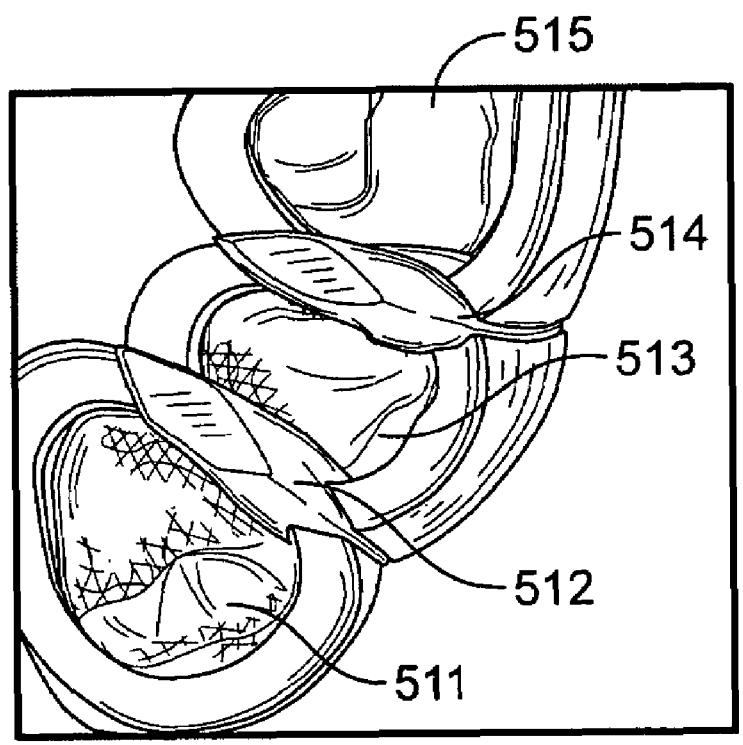
Figure 17:
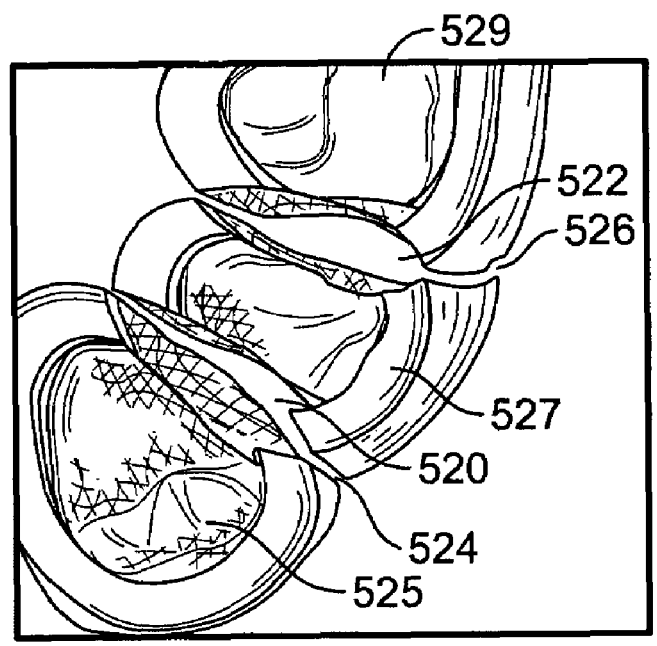
Figure 18:
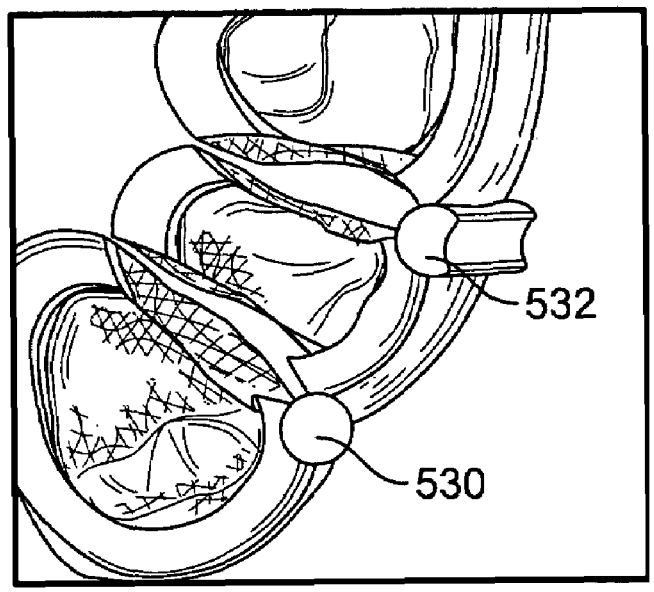
Figure 19:
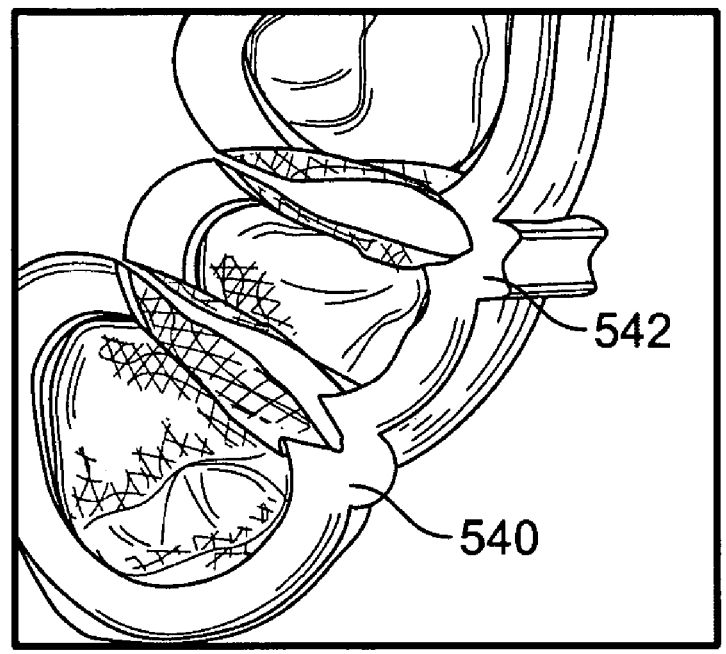

FIGS. 15 and 16 illustrate the need to remove the common volume 510 from adjacent tooth models. FIG. 15 illustrates the subtraction of original tooth models of FIG. 9 from scaled tooth models of FIG. 10 to form cavities 509 that are separated by the sentum 510. Such formations would preclude the template from being placed over a patient's teeth. In FIG. 16, the common volumes 512 and 514 are positioned between the tooth model 511 and the tooth model 513 and between the tooth model 513 and the tooth model 515. The volumes 512 and 514 are shown prior to their removal or subtraction. FIG. 17 illustrates models with common volumes removed from the template model. In this case, the common volumes 520 and 522 are enlarged for clarity but in practice at volume size it would be defined by the scaling factor of the teeth that lead to the common volume shape. FIGS. 18 and 19 show the addition of buttresses or means for connecting disjoint tooth models. Referring back to FIG. 17, once those common volumes 520 and 522 have been removed, gaps 524 and 526 may exist between the tooth models 525, 527 and 529, respectively.

FIGS. 18-19 show a formation of a solid body that is one continuous template to be positioned on a patient's teeth. In the case of FIG. 18, the joining elements or buttress elements 530-532 are inserted as separate bodies after the creation of the template model. Buttress element 530 is a circular element, while buttress element 532 is a crescent shaped element. These represent two possibilities for shapes, many others are possible. The surfaces of the buttress elements are joined to the surfaces of the template model. FIG. 19 shows the addition of buttressing elements 540-542 subsequent to the above operation for forming cavities. In this operation, one continuous body which is comprised of the three tooth models as well as the buttressing elements 540-542, is formed all at once. In both cases, the buttress elements are built into the template model. Subsequent steps may be taken to further shape the template model or elements thereof.

Pseudo-code for generating a template using the tooth scaling approach is as follows:

1. A digital representation of a tooth is acquired through scanning or other digitization means.
2. This tooth file is opened in a computer application that allows a user to alter it or that itself alters the file.
3. The tooth is enlarged to a scale greater than 100%—typically in the range of 105 to 150%; and saved as a separate file.
   The original tooth file (i.e. 100% scales) is co-located within the scaled tooth.
   The original tooth's geometry is subtracted from that of the scaled tooth to leave a hollowed or shelled body.
   The root and other sub-gingival aspects are removed from this body. The removal can be performed through the use of additional bodies or surfaces that cut, cavity, or are subtracted from the body to be kept.
   Adjacent Tooth Cavity Method A.
   Solid (not hollow), scaled versions of adjacent teeth are subtracted from this body where the bodies overlap or intersect.
   Adjacent Tooth Cavity Method B.
   The geometry common to the object tooth and adjacent teeth is subtracted from this body. This step is best performed before the hollowing of the object tooth.
4. All teeth in the target arch which are to be part of the template are then brought together in their proper relative positions and orientations to form the template for this arch.
5. Exterior interproximal regions are filled in, as needed, to join the tooth shell segments together. This 'buttressing' process has numerous possibilities, among them:
   Add a solid body that extends beyond the teeth's buccal surfaces and re-cavity it where it would otherwise collide with the teeth.
   Individually fill the interproximal regions between adjacent teeth outward from the buccal surfaces of the 100% and/or scaled teeth.
   Add another, larger-scaled tooth over each respective tooth and re-cavity it where it would otherwise collide with the underlying tooth.
   Allow the interproximal regions to be disjoint, but connect the individual teeth by applying a solid body on and into the incisal/occlusal surfaces. Re-cavity this as necessary.
6. Any unwanted or interfering geometries are removed. This may include the positions for brackets or other orthodontic or dental components. As noted above, the removal can be performed through the use of additional bodies or surfaces that are used to cut, cavity, or subtract from the kept body/bodies.
7. If necessary, the resultant file is converted to a format required by the rapid-prototyping method.

Figure 20:
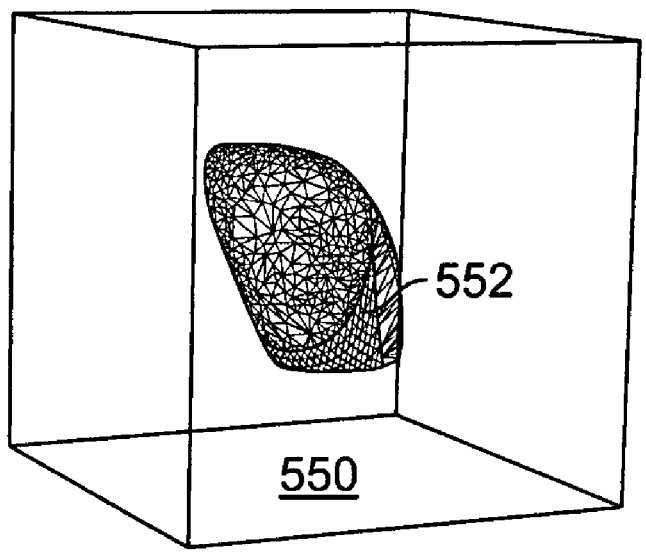
Figure 21:
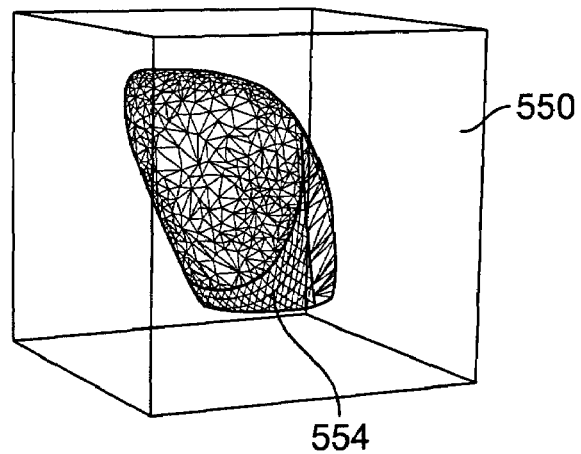
Figure 22:
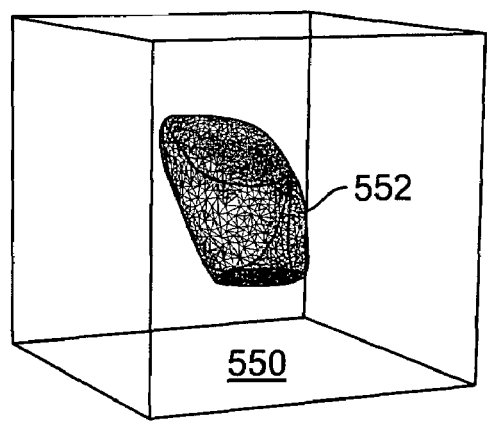
Figure 23:
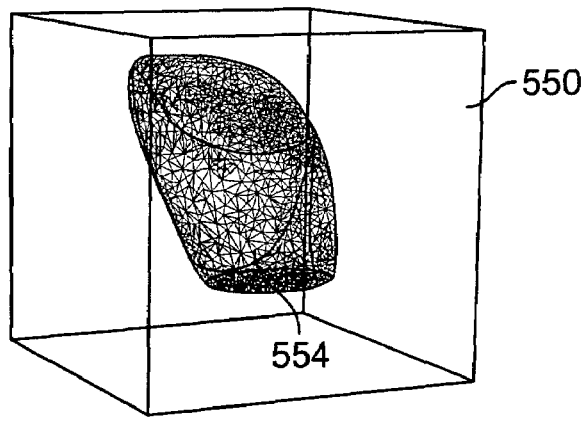
Figure 24:
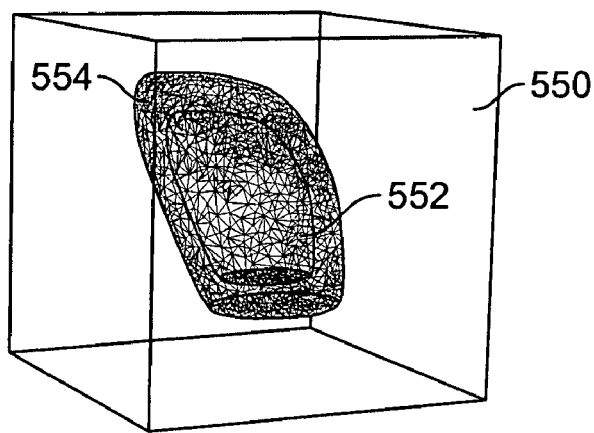

FIGS. 20-27 show various diagrams illustrating an overlaid cavities embodiment. In FIG. 20, a block 550 is used as an arbitrary body and a 100% scaled tooth model 552 has been placed inside that body. In FIG. 21, the same block 550 with the same dimensions in every aspect as the body of block 550 in FIG. 20 contains a scaled tooth 554 (such as a 140% scaled tooth model). In each case, the body fully encompasses the original and scaled tooth models. In FIG. 22, the 100% tooth has been cavitied or hollowed from the block 550, and in FIG. 23, the 140% scaled tooth model 554 is cavitied from the block 550. In FIG. 24, the cavitied block 550 that contained the 100% tooth model 552 is co-located with the cavitied block 550 that contained the 140% tooth model 554 so that the model 552 is inside the model 554.

Figure 25:
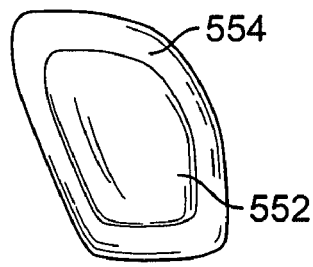
Figure 26:
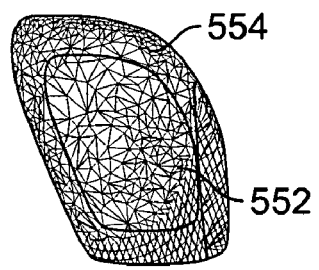
Figure 27:
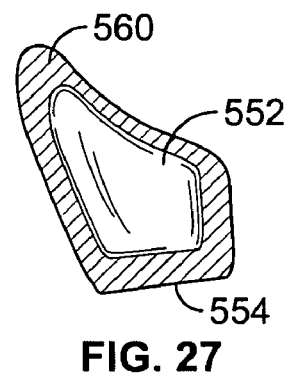

FIG. 25 shows a subtraction of the cavity blocks 550 for the 100% tooth model and the cavity block 550 for the scaled tooth model to create a body defined by the area between the 100% scale and the 140% scale models 552 and 554, respectively. A wire frame model of the scaled tooth model 554 with a solid model of the original 100% tooth model 552 is shown in FIG. 26. FIG. 27 is a cross sectional view of the models of FIG. 26 to show a shell 560 that surrounds the 100% scaled tooth model 552 with the outer surface being defined by the scaled tooth model 554.

Pseudo code for performing the overlaid cavity embodiment is as follows:

1. A digital representation of a tooth is acquired through scanning or other digitization means.
2. This tooth file is opened in a computer application that allows a user to alter it or that itself alters the file.
3. A body that more than encompasses the space occupied by all the teeth is created or opened in the application. This is Block 550 in the images. Alternately, encompassing bodies may be created for an individual tooth or groups of teeth. These bodies would later be brought together into one template file (FIG. 20).
4. Preferentially, all object teeth are moved into this file into their proper positions and orientations. The body is then cavitied with the teeth. Alternately, the body could be successively cavitied by individual teeth. The resultant body is saved.
5. Each tooth is then enlarged to a scale greater than 100%—typically in the range of 105 to 150%; and saved as a separate file.
6. A second, identical, all-encompassing body (550) is created or opened in the application (FIG. 21).
7. Step 4 is repeated for Block 550 (FIG. 21) with the difference being that the scaled teeth of Step 5 are used. Alternately, it is not required to create and use scaled teeth. Rather, the original teeth may be cavitied in Block 550 at a larger than 100% scale.
8. Block 550 of FIG. 20 and Block 550 of FIG. 21 are co-located in one of their files or in a new file that preferentially contains only these two objects.
9. Block 550 of FIG. 21 is subtracted from Block 550 of FIG. 20. This leaves one or more shelled bodies—the exterior surfaces defined by the scaled teeth and the interior surfaces by the original, unscaled teeth.
10. The roots and sub-gingival aspects are removed from the body/bodies. The removal can be performed through the use of additional bodies or surfaces that cut, cavity, or are subtracted from the body to be kept.
11. Successively or contemporaneously, the geometry common to an object tooth and its adjacent teeth is subtracted from the body/bodies.

12. Exterior interproximal regions are filled in, as needed, to join the tooth shell segments together. This 'buttressing' process has numerous possibilities:

Add a solid body that extends beyond the teeth's buccal surfaces and re-cavity it where it would otherwise collide with the teeth.

Individually fill the interproximal regions between adjacent teeth outward from the buccal surfaces.

Add another, larger-scaled tooth over each respective tooth and re-cavity it where it would otherwise collide with the underlying tooth.

Allow the interproximal regions to be disjoint, but connect the individual teeth by applying a solid body on and into the incisal/occlusal surfaces. Re-cavity this as necessary.

The buttressing can be placed or enacted on the scaled teeth prior to, at the same time as, or subsequent to Steps 7 and/or 8. It is preferentially performed prior to Step 9.

13. Any unwanted or interfering geometries are removed, e.g. internal interproximal regions. This removal may include the positions for brackets or other orthodontic or dental components. The removal can be effected as described above.

14. If necessary, the resultant file is converted to a format required by the rapid-prototyping method.

Figure 28:
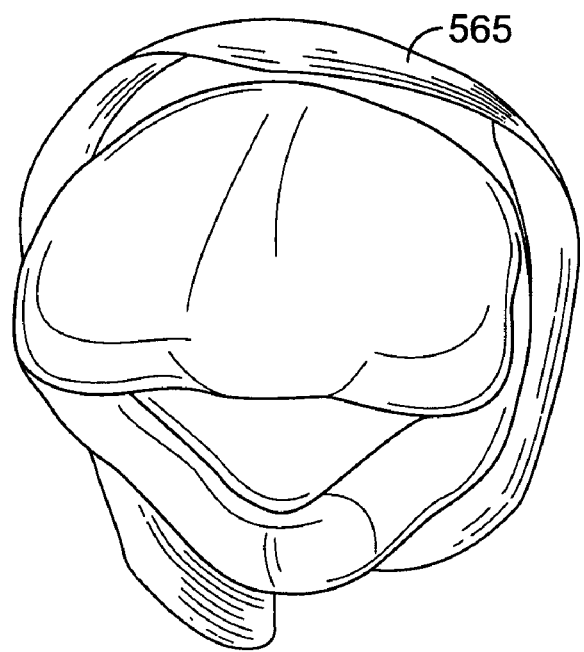
Figure 29:
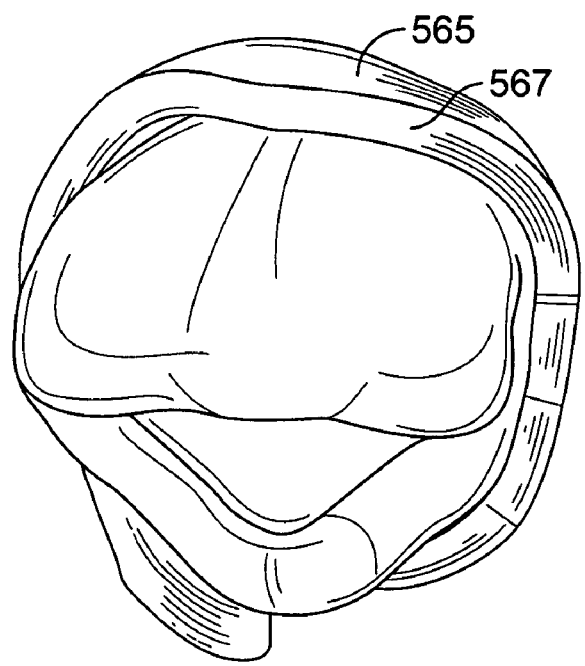
Figure 30:
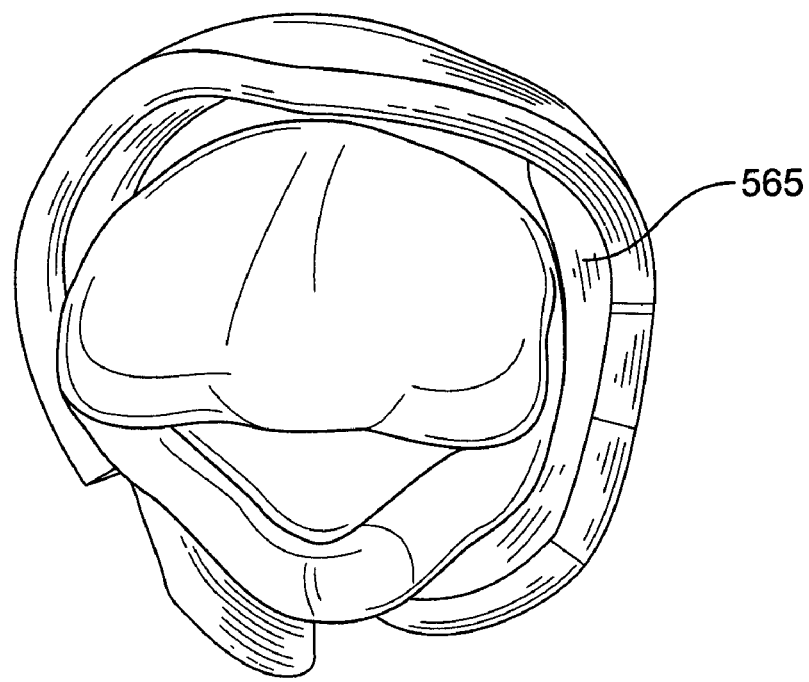
Figure 31:
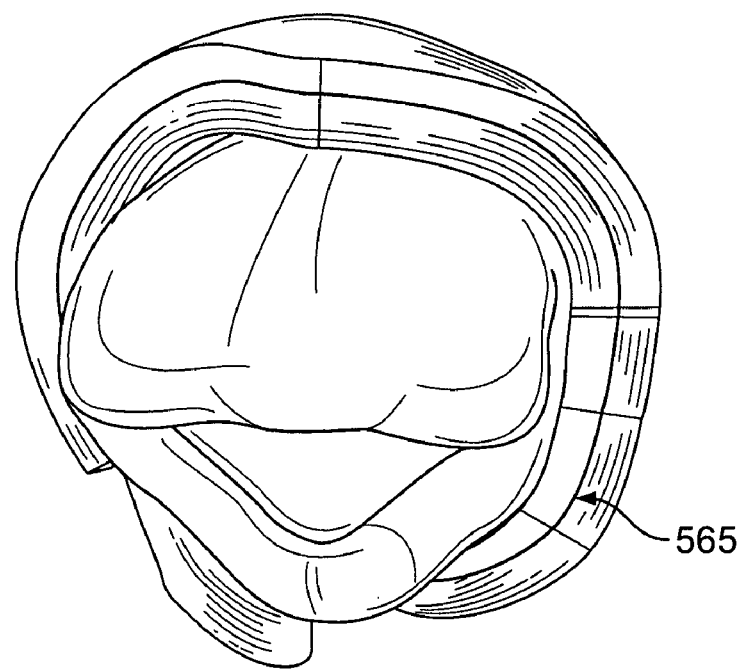
Figure 32:
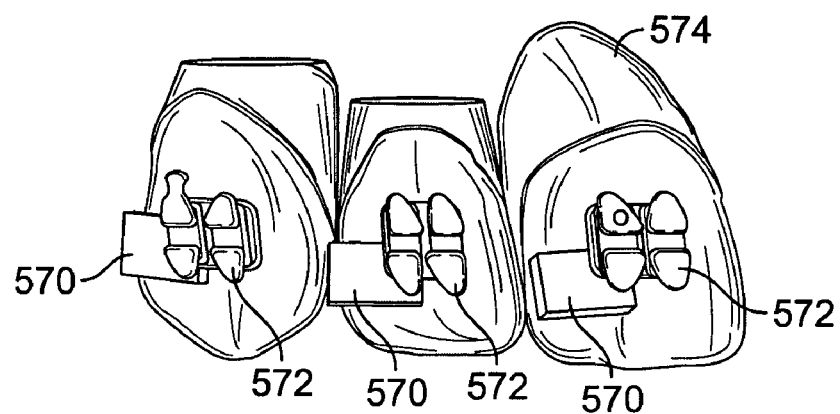

FIG. 28 illustrates another embodiment for scaling a tooth model. In this embodiment, the original tooth model surface is off-set (565) using a predetermined mathematical formula or predetermined points or constraints. The embodiment off-sets numerous surfaces to show alternative methods to enlarging the tooth model or creating a surface that bounds the same shape but in a large scale of the tooth model. FIG. 29 thickens the surface (565) from FIG. 28 inward towards the tooth to form body 567. FIG. 30 is that same surface (565) but now thickening it outward away from the tooth, and FIG. 31 is showing thickening both inward and outward at the same time.

Figure 33:
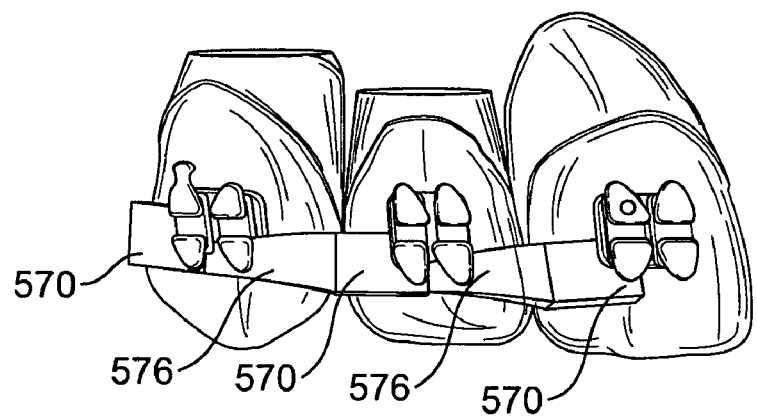
Figure 34:
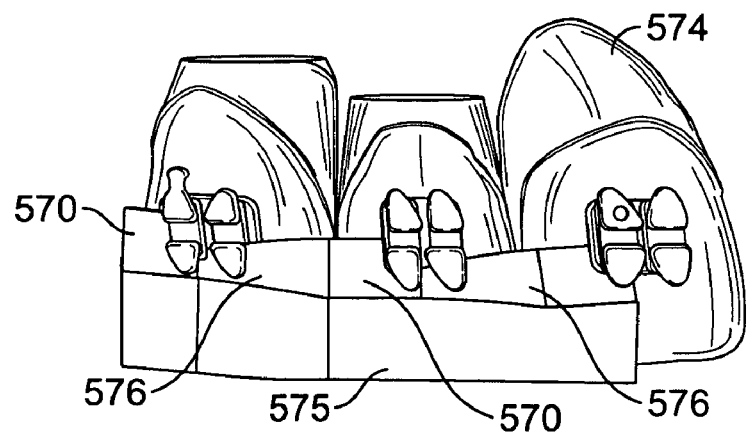
Figure 35:
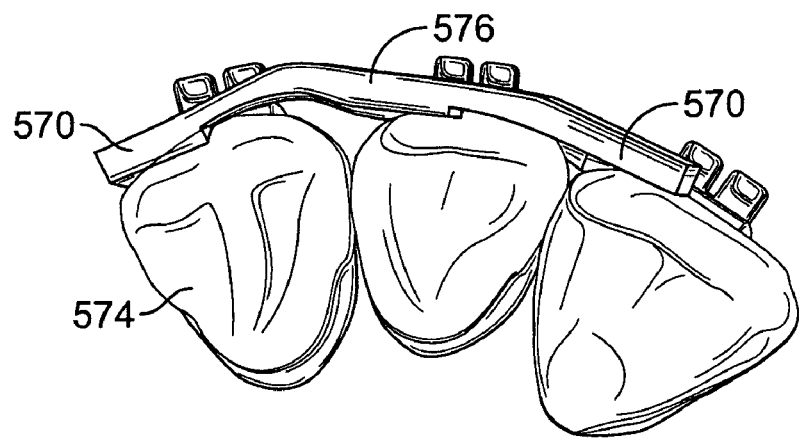

FIGS. 32-35 show another embodiment for creating a template. In this embodiment, a geometric body 570 (FIG. 32) is placed so that it abuts an orthodontic component 572 on a tooth 574. In one embodiment, the component 572 is a bracket. The bracket position defines where this added body lies; in this case the corner of the body 570 abuts the bracket 572 on two sides. In the embodiment of FIGS. 32-35, three brackets have been placed and three geometric bodies are positioned against the brackets 572 in FIG. 32. In FIG. 33, bodies 570 are joined with the two joining elements 576 between bodies 570. In FIG. 34 the structure of FIG. 33 is extended up to or beyond the teeth, for example—the incisor or occlusal surfaces. FIGS. 34-35 show an occlusal view as well as a buccal view of the bodies 570 and joining elements 576 on teeth 574. In FIGS. 34-35, an extended body 575 is linked to the bodies 570 and 576, to extend the height of the attachment combination.

Figure 36:
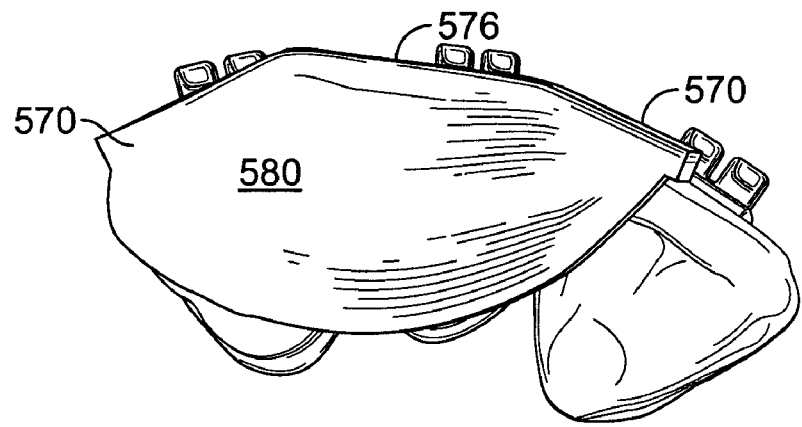
Figure 37:
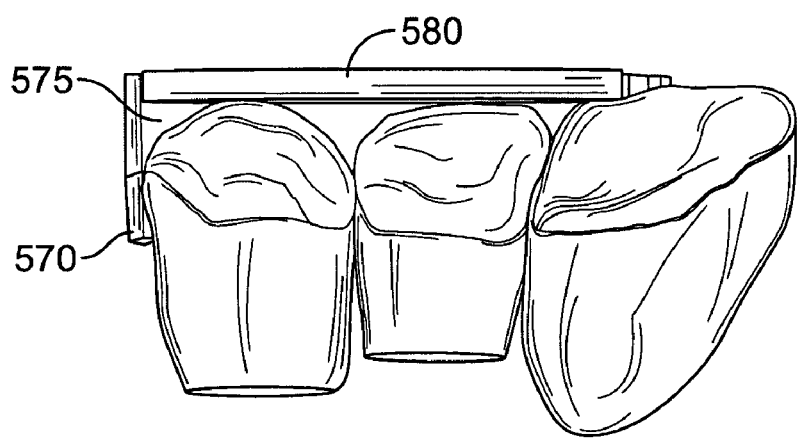

FIGS. 36 and 37 show that once the bodies 570 have been extended as shown in FIGS. 34 and 35, an additional coverage body 580 can be positioned over the occlusal or incisal surfaces to fully define where the template is in space relative to the teeth and in this case a simple plate shape is shown. However, more complex geometries can be used.

Pseudo-code for the Tooth Plating embodiment is as follows:
1. A digital representation of a tooth is acquired through scanning or other digitization means.
2. This tooth file is opened in a computer application that allows a user to alter it or that itself alters the file.
3. The orthodontic or dental component is placed on the tooth in its intended position. Alternately, the plate is placed with respect to where it is known the component will be placed.
4. A body is placed on, into, and/or over the tooth so it abuts the component with contact sufficient to limit its degrees of freedom as desired. This body may be a standardized shape or customized relative to tooth type or specifically to a given patient's tooth or teeth. At minimum, this body will have these characteristics or features: a buccolingual thickness greater than approximately half the this dimension of the component, but generally less than the sum of the thicknesses of the component and its respective tooth; a mesiodistal length that may be greater than, less than, or equal to the tooth's mesiodistal width; and an occlusogingival height that may be greater than, less than, or equal to the height of the tooth. The body could be simply rectalinear or as complex as the tooth or mouth morphology and could also include a mating cavity for the orthodontic component. Or the component could subsequently be cavitied in the body when the latter is merely approximately positioned.
5. After all teeth have been 'plated', the plates are merged, connected, or joined where there are gaps and cut, trimmed, or shaped where they are undesirably protrusive. An incisal/occlusal element could also be merged into the plates at this time.
6. If necessary the tooth bodies are subtracted from the body comprised of the plates and any incisal/occlusal element.
7. Any unwanted or interfering geometries are removed. This may include the positions for brackets or other orthodontic or dental components. See above for methods of removal.
8. If necessary, the resultant file is converted to a format required by the rapid-prototyping method.

Figure 38:
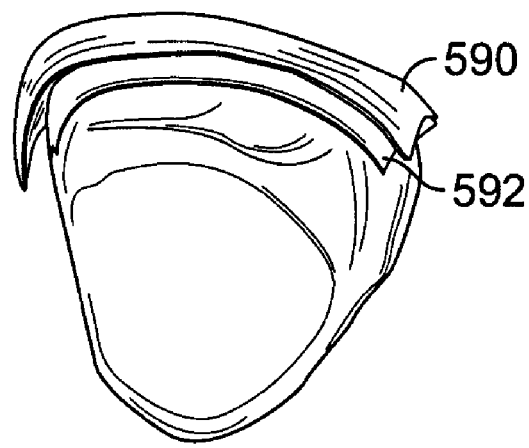
Figure 39:
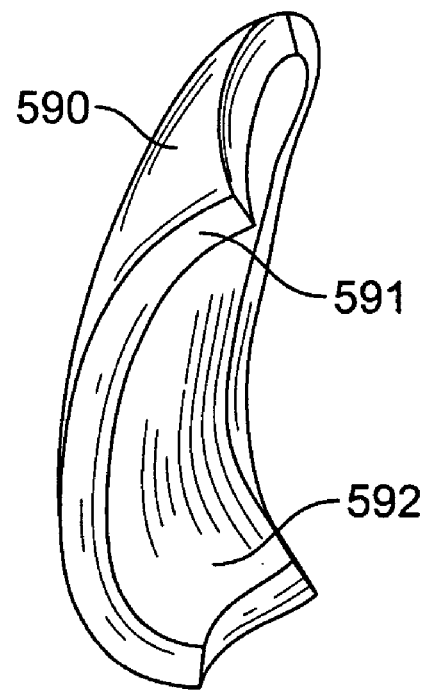

FIGS. 38 and 39 show another embodiment of the surface off-set method. In this embodiment, two surfaces 590 and 592 are used rather than just one surface. In FIG. 38, one surface 592 is offset at or near the tooth. A second surface 590 is offset at a distance larger than the distance from surface 592 resulting in two surfaces that are essentially congruent but located at a different distance. FIG. 39 shows the two surfaces 590 and 592 bounding a solid body. The solid body can be specified in a number of ways. For example, one surface can be extruded towards the other surface alternatively, the edges (591) where the surfaces gap can be closed.

Pseudo-code for Surface Off-setting is as follows:
1. A digital representation of a tooth is acquired through scanning or other digitization means
2. This tooth file is opened in a computer application that allows a user to alter it or that itself alters the file.
3. The surface(s) of the tooth is offset to a desired distance.
4. This surface is thickened in a radially outward direction if the offset distance is greater than zero. The surface is thickened in a radially inward or inward and outward if the distance is greater than zero. The inwardly directed thickness preferentially does not penetrate the surface of the tooth. However, if it does, the tooth body could be subsequently subtracted from the solid created by thickening the offset surface(s).
5. Any unwanted or interfering geometries are removed. These may include the interproximal areas as well as the positions for brackets or other orthodontic or dental components. See above for removal methods.
6. If necessary, the resultant file is converted to a format required by the rapid-prototyping method.

Pseudo-code for Multiple Surface Off-setting is as follows:
1. A digital representation of a tooth is acquired through scanning or other digitization means.
2. This tooth file is opened in a computer application that allows a user to alter it or that itself alters the file.
3. The surface(s) of the tooth is offset to a desired first distance.
4. The surface(s) of the tooth is offset to a second desired distance, preferentially greater or less than the first distance.
5. The volume between the first and second surfaces is then filled to create a solid body.
6. If one of the offset distances sets the corresponding surfaces inside the tooth body, the solid body can be cavitied with the original tooth body.
7. Any unwanted or interfering geometries are removed. These may include the interproximal areas as well as the positions for brackets or other orthodontic or dental components. See above for removal methods.
8. If necessary, the resultant file is converted to a format required by the rapid-prototyping method.

Figure 40:
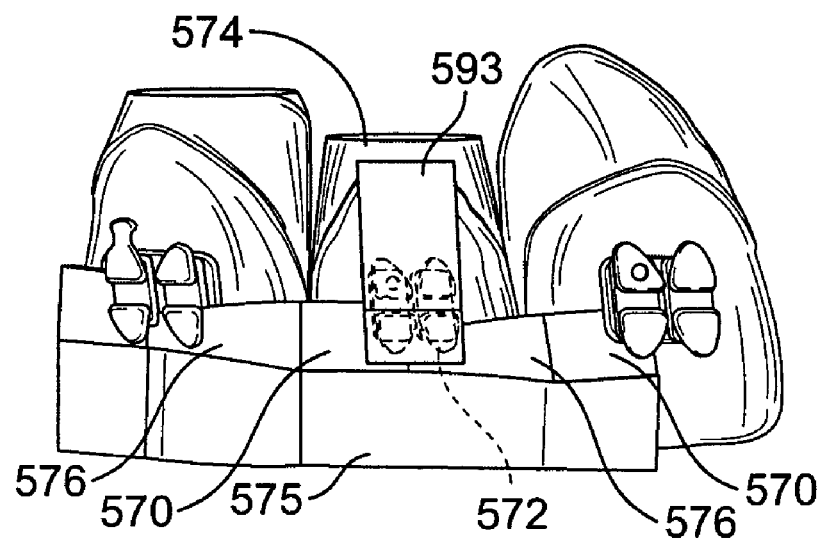
Figure 41:
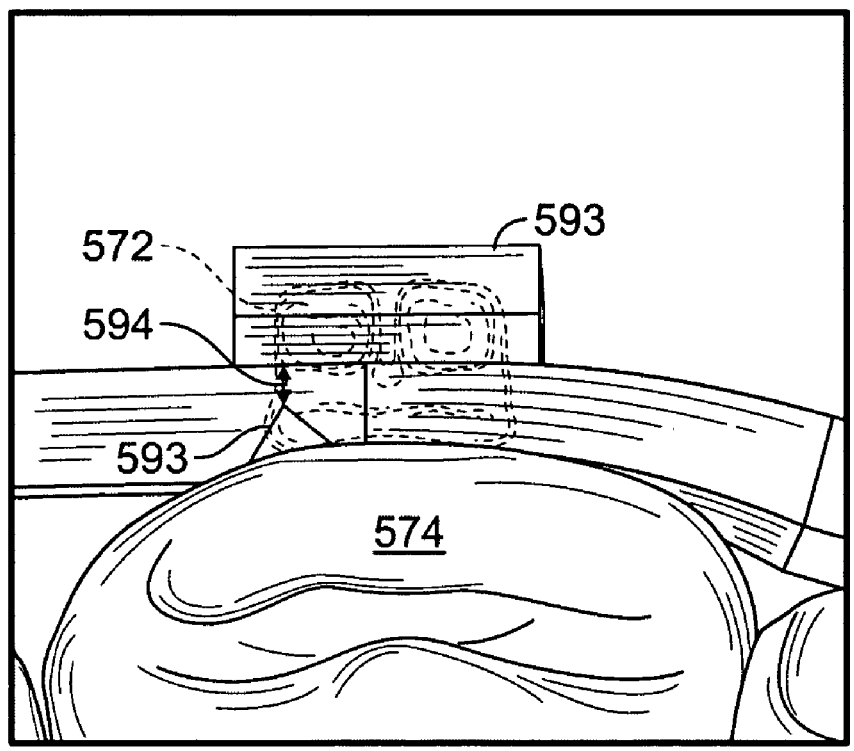

FIGS. 40 and 41 show one embodiment of template cutting. A cutting body 593 partially encompasses the underlying bracket 572 to create a 'window' in the template wherein the bracket can be positioned and affixed while still allowing for subsequent removal of the template. In one embodiment, the cutting body 593 has a simple geometry. Other shapes could encompass more or less of the underlying orthodontic or dental component based on need or intent. Further, the shape of the body 593 could be more complex to create additional benefits such as a partial lock to hold the component 'hands free' in place, cause a seam along which the template is readily broken for removal, or allow for easier access for bonding or curing. In this example, the encompassing body 593 continues lingual to the to-template's buccal surface to cause a sharp-edged thin area 594 along whose buccal edge it is made easier to break the template.

The body 593 creates a cutout in the template to position an orthodontic or dental component such as a bracket. It may not be necessary to capture all the geometry, rather to capture aspects of the geometry sufficient to locate that bracket or component in the right location. In this case, the central tooth has a body over the bracket. This body extends gingivally beyond the bracket body so the bracket can be placed in the template and bonded on the tooth and subsequently the template can be removed.

FIG. 41 is an occlusal view of the same bracket, body, and template portion but showing other features that can be incorporated in the body. In this case, there is a triangular aspect in cutting body 593 that will cut into the template to create a breaking edge 594 or a break away line. More complex geometries can be used for severely rotated or severely tipped teeth since there might need to be different access paths to position one or more of the components and that may also facilitate template removal.

The above templates can also position the bracket in any arbitrary 3D position to support a predetermined angulation and inclination specification for a bracket. In that case, the template would fix the bracket in space relative to the tooth.

Various alternatives, modifications, and equivalents may be used in lieu of the above components. Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner. Further, while the invention has been shown and described with reference to an embodiment thereof, those skilled in the art will understand that the above and other changes in form and detail may be made without departing from the spirit and scope of the following claims.

What is claimed is:

1. A method of fabricating a dental template to position an object on a patient's tooth, comprising:
creating a model of said patient's tooth;
adding one or more objects to predetermined locations on the tooth model;
moving at least one object to a predetermined inclination and/or a predetermined angulation;
scaling the tooth model;
superimposing the scaled tooth model over the original tooth model; and
fabricating the dental template to locate the object on the patient's tooth with the predetermined inclination and/or angulation.

2. The method of claim 1, further comprising placing a virtual object on the superimposed scaled tooth model.

3. The method of claim 1, further comprising placing a virtual object at a predetermined location and orientation in the superimposed scaled tooth model.

4. The method of claim 1, further comprising removing the tooth model from the scaled tooth model to form a virtual appliance.

5. The method of claim 1, further comprising removing a digitized structure from a virtual object at a distance along the gingival line or lines.

6. The method of claim 1, further comprising removing structure in proximal contact with an adjacent tooth.

7. The method of claim 1, wherein the tooth model is either a physical model or a digital model.

8. The method of claim 1, wherein fabricating comprises rendering a physical dental template using a rapid prototyping method.

9. A method of placing an orthodontic object on a patient's tooth, comprising:
digitizing the patient's tooth;
adding a virtual object to a predetermined location on the digitized tooth;
moving the virtual object to a predetermined inclination and/or a predetermined angulation;
scaling the digital tooth;
superimposing the scaled digital tooth over the digital tooth;

fabricating the dental template to locate the object on the patient's tooth with the determined inclination and/or angulation;
mounting the orthodontic object on the template;
placing the template on the patient's teeth; and
bonding the orthodontic object to the tooth.

10. The method of claim 9, further comprising placing the virtual object in the superimposed scaled digital tooth.

11. The method of claim 9, further comprising placing the virtual object at a predetermined location and orientation in the superimposed scaled digital tooth.

12. The method of claim 9, further comprising placing the virtual object at a predetermined location and orientation in the superimposed scaled digital tooth.

13. The method of claim 9, further comprising removing digitized structures at a distance from the gingival line or lines.

14. The method of claim 9, further comprising removing digitized structures in direct interproximal contact with or undesirable proximity to an adjacent tooth.

15. The method of claim 9, further comprising removing buccal, gingival, or lingual structures.

16. The method of claim 9, wherein fabricating comprises rendering a physical dental template using a rapid prototyping method.

17. The method of claim 9, further comprising removing overlapping structure between two teeth.

18. The method of claim 9, further comprising removing overlapping volume between two teeth.

19. The method of claim 9, further comprising removing overlapping space between two teeth.

* * * * *

UNITED STATES PATENT AND TRADEMARK OFFICE
CERTIFICATE OF CORRECTION

PATENT NO. : 7,658,610 B2
APPLICATION NO. : 10/794324
DATED : February 9, 2010
INVENTOR(S) : Peter G. Knopp Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1076 days.

Signed and Sealed this

Thirtieth Day of November, 2010

David J. Kappos
*Director of the United States Patent and Trademark Office*